US012727944B2

(12) United States Patent
Benson et al.

(10) Patent No.: US 12,727,944 B2
(45) Date of Patent: Sep. 8, 2026

(54) SYSTEM AND METHOD FOR PLANNING AND VALIDATING A PROCEDURE

(71) Applicant: Medicrea International, Rillieux la Pape (FR)

(72) Inventors: Nicolas M. Benson, Collierville, TN (US); Thomas Mosnier, Saone (FR); Adam Deitz, Austin, TX (US); Joseph Moctezuma, Winter Park, CO (US); Christopher Ames, Mill Valley, CA (US)

(73) Assignee: Medicrea International, Rillieux la Pape (FR)

( * ) Notice: Subject to any disclaimer, the term of this patent is extended or adjusted under 35 U.S.C. 154(b) by 226 days.

(21) Appl. No.: 18/172,953

(22) Filed: Feb. 22, 2023

(65) Prior Publication Data

US 2024/0277412 A1 Aug. 22, 2024

(51) Int. Cl.

| | |
|---|---|
| ***A61B 34/10*** | (2016.01) |
| ***A61B 17/00*** | (2006.01) |
| ***G06T 17/00*** | (2006.01) |
| ***G06T 19/20*** | (2011.01) |

(52) U.S. Cl.

CPC .............. *A61B 34/10* (2016.02); *G06T 17/00* (2013.01); *G06T 19/20* (2013.01); *A61B 2017/00725* (2013.01); *A61B 2034/102* (2016.02); *A61B 2034/108* (2016.02); *G06T 2200/24* (2013.01); *G06T 2210/41* (2013.01); *G06T 2219/2004* (2013.01); *G06T 2219/2016* (2013.01)

(58) Field of Classification Search

None

See application file for complete search history.

(56) References Cited

U.S. PATENT DOCUMENTS

| | | | | |
|---|---|---|---|---|
| 8,238,631 | B2 | 8/2012 | Hartmann et al. | |
| 9,737,235 | B2 | 8/2017 | Hartmann | |
| 10,881,371 | B2 | 1/2021 | Helm et al. | |
| 11,071,507 | B2 | 7/2021 | Helm et al. | |
| 11,135,025 | B2 | 10/2021 | Snyder et al. | |
| 11,547,491 | B2 | 1/2023 | Wolfsberger | |
| 2010/0228117 | A1 | 9/2010 | Hartmann | |
| 2010/0290690 | A1 | 11/2010 | Hartmann et al. | |
| 2012/0099772 | A1 | 4/2012 | Helm et al. | |
| 2012/0250822 | A1 | 10/2012 | Helm et al. | |
| 2017/0312031 | A1* | 11/2017 | Amanatullah | A61B 34/10 |
| 2019/0380782 | A1* | 12/2019 | McAfee | A61B 34/10 |
| 2020/0253666 | A1* | 8/2020 | Spaelter | A61B 90/37 |
| 2020/0315553 | A1 | 10/2020 | Helm et al. | |
| 2021/0169578 | A1 | 6/2021 | Calloway et al. | |
| 2021/0393330 | A1* | 12/2021 | Barut | G06T 3/40 |

(Continued)

FOREIGN PATENT DOCUMENTS

WO 2022161626 A1 8/2022

OTHER PUBLICATIONS

International Search Report and Written Opinion for related International Application No. PCT/IB2024/000076; Date of Mailing: May 22, 2024; 15 pages.

*Primary Examiner* — Jeffrey J Chow

(74) *Attorney, Agent, or Firm* — Harrity & Harrity, LLP

(57) ABSTRACT

A method and system is disclosed for displaying image data of a subject and a model. The model may include an implant or item model. The model may be used to assist in validation of a procedure.

20 Claims, 15 Drawing Sheets

(56) References Cited

U.S. PATENT DOCUMENTS

| | | | | |
|---|---|---|---|---|
| 2022/0287676 | A1* | 9/2022 | Steines | A61B 6/102 |
| 2023/0290085 | A1* | 9/2023 | Lo | G06T 19/006 |
| 2023/0404671 | A1* | 12/2023 | Stambouzou | G16H 30/40 |
| 2024/0058064 | A1* | 2/2024 | Weiser | A61B 34/20 |
| 2024/0138931 | A1* | 5/2024 | Lefauconnier | A61B 17/7011 |
| 2024/0245375 | A1* | 7/2024 | Wollowick | G06T 7/0014 |
| 2024/0261029 | A1* | 8/2024 | Casey | A61B 34/10 |
| 2024/0315741 | A1* | 9/2024 | Lefauconnier | A61B 90/39 |
| 2024/0319709 | A1* | 9/2024 | Roh | G16H 50/20 |

* cited by examiner

| Anatomy | Pre-Op | Plan |
|---|---|---|
| Pelvic Tilt, PT (*) | 32 | 23 |
| Pelvic Incident, PI (*) | 63 | 63 |
| Sacral Slope, SS (*) | 31 | 40 |
| Lumbar Lordosis, LL (*) | 16 | -52 |
| L1-L4 Lordotic Distribution(%) | 0 | 33 |
| L4-S1 Lordotic Distribution(%) | >100 | 67 |
| PI-LL (*) | 47 | 11 |
| Sagittal Vertical Axis,SVA(mm) | 116 | 10 |
| T4-T12 Thoracic Kyphosis, TK (*) | PlanA 32 | 32 |

| Anatomy | Plan | Image |
|---|---|---|
| Pelvic Tilt, PT (*) | Plan A 23 | 22 |
| Pelvic Incident, PI (*) | PlanA 63 | 60 |
| Sacral Slope, SS (*) | PlanA 40 | 45 |
| Lumbar Lordosis, LL (*) | PlanA -52 | -55 |
| L1-L4 Lordotic Distribution(%) | PlanA 33 | 30 |
| L4-S1 Lordotic Distribution(%) | PlanA 67 | 65 |
| PI-LL (*) | PlanA 11 | 8 |
| Sagital Vertical Axis,SVA(mm) | PlanA 13 | 10 |
| T4-T12 Thoracic Kyphosis, TK (*) | PlanA 32 | 29 |

SYSTEM AND METHOD FOR PLANNING AND VALIDATING A PROCEDURE

FIELD

The present disclosure relates to imaging a subject, and particularly to a system to acquire image data and for generating a selected view of the subject regarding a procedure.

BACKGROUND

This section provides background information related to the present disclosure which is not necessarily prior art.

A subject, such as a human patient, may undergo a procedure. The procedure may include a surgical procedure to correct or augment an anatomy of the subject. The augmentation of the anatomy can include various procedures, such as movement or augmentation of bone, insertion of an implant (i.e., an implantable device), or other appropriate procedures.

A surgeon can perform the procedure on the subject with images of the subject that are based on projections of the subject. The images may be generated with one or more imaging systems such as a magnetic resonance imaging (MRI) system, a computed tomography (CT) system, a fluoroscopy (e.g., C-Arm imaging systems).

SUMMARY

This section provides a general summary of the disclosure, and is not a comprehensive disclosure of its full scope or all of its features.

According to various embodiments, a system to acquire image data of a subject may be any appropriate imaging system. The imaging system may acquire image data with x-rays, magnetic resonance, etc. The image data may be two dimensional (2D) or three dimensional (3D). The images may be 2D or 3D that are reconstructed or generated with the selected image data. The subject may be a living patient (e.g., a human patient). The subject may also be a non-living subject, such as an enclosure, a casing, etc. Generally, the imaging system may acquire image data of an interior of the subject. The imaging system may include a moveable source and/or detector that is moveable relative to the subject.

An imaging system may include a movable source and/or detector to create a plurality of projections of a subject and/or generate 3D image data. In various embodiments, a plurality of projections may be acquired in a linear path of movement of the source and/or detector. The plurality of projections may then be combined, such as by stitching together, to generate or form a long view (also referred to as a long film). The long view may be a 2D view of the subject. In various embodiments, however, the long film may also be a 3D image. The 3D image may be reconstructed based on image data acquired with the imaging system.

Imaging system(s) to collect image data may include those disclosed in U.S. Pat. No. 10,881,371 to Helm et al., incorporated herein by reference. Imaging system(s) to collect image data may include those disclosed in U.S. patent application Ser. No. 17/887,599 filed Aug. 15, 2022, incorporated herein by reference. In addition, various system (s) may be used to track and illustrate a pose of one or more tracked portions relative to a displayed image, such as those disclosed in U.S. Pat. Nos. 11,135,025 and 11,547,491, incorporated herein by reference.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

A subject may be imaged with an imaging system, as discussed further herein. The subject may be a living subject, such as a human patient. Image data may be acquired of the human patient and may be combined to provide an image of the human patient that is greater than any dimension of any single projection acquired with the imaging system. It is understood, however, that image data may be acquired of a non-living subject, such an inanimate subject including a housing, casing, interior of a super structure, or the like. For example, image data may be acquired of an airframe for various purposes, such as diagnosing issues and/or planning repair work.

Image data of the subject may be used for various purposes. For example, the image data may be used to generate an image to assist in planning a procedure, such as selecting or planning an implant. A generated or reconstructed image may be used to plan and create the implant. In planning the implant, a model, such as a computer aided design (CAD) model (also referred to herein an implant model) may be generated and include or have saved specific dimensions (e.g., length, width, volume) and geometry (e.g., angles, length between one or more angles). The image and/or the model may be used to assist in performing and/or validating a procedure.

Figure 1:
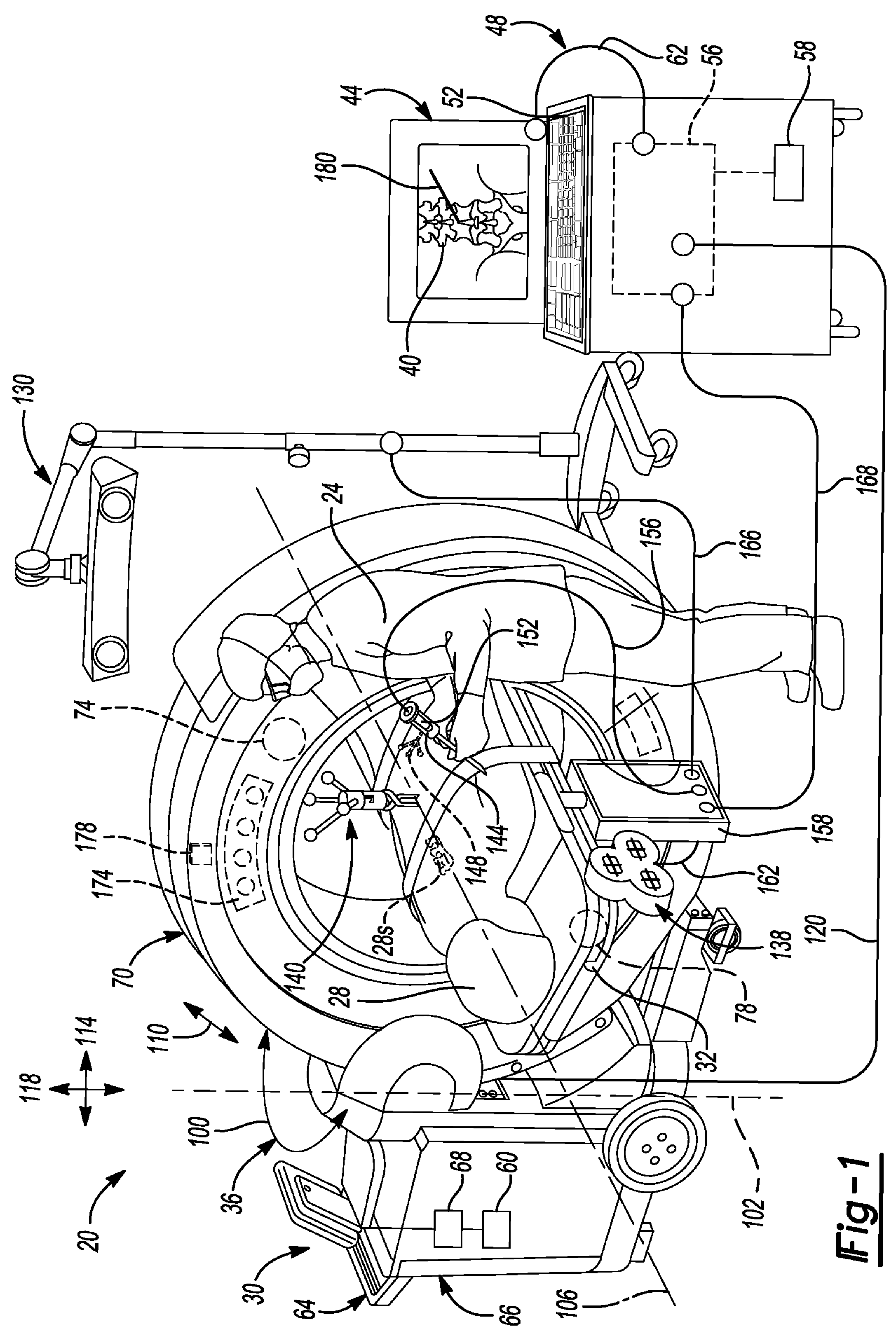
FIG. 1 is an environmental view of an imaging system in an operating theatre.

With reference to FIG. 1, a schematic view of a procedure room 20 is illustrated. A user 24, such as a surgeon, can perform a procedure on a subject, such as a patient 28. The subject may be placed on a support, such as a table 32 for a selected portion of the procedure. The table 32 may not interfere with image data acquisition with an imaging system 36. In performing the procedure, the user 24 can use the imaging system 36 to acquire image data of the patient 28 to allow a selected system to generate or create images to assist in performing a procedure. Images generated with the image data may be two-dimensional (2D) images, three-dimensional (3D), or appropriate type of images, such as a generated or reconstructed subject model (such as a three-dimensional (3D) image that may be reconstructed with the image data and/or the image data is used to morph a standard model), long views, single projections views, etc. can be generated using the image data and displayed as an image 40 on a display device 44. The display device 44 may be part of and/or connected to a processor system 48 that includes an input device 52, such as a keyboard, and a processor 56, which can include one or more processors, processor module, and/or microprocessors incorporated with the processing system 48 along with selected types of non-transitory and/or transitory memory 58. A connection 62 can be provided between the processor 56 and the display device 44 for data communication to allow driving the display device 44 to display or illustrate the image 40. The processor 56 may be any appropriate type of processor such as a general-purpose processor that executes instructions included in a program or an application specific processor such as an application specific integrated circuit.

The imaging system 36 may be an O-Arm® imaging system sold by Medtronic Navigation, Inc. having a place of business in Louisville, CO, USA. The imaging system 36, including the O-Arm® imaging system, or other appropriate imaging systems may be in use during a selected procedure, such as the imaging system described in U.S. Patent App. Pubs. 2012/0250822, 2012/0099772, and 2010/0290690, all the above incorporated herein by reference. Further, the imaging system may include various features and elements, such as a slotted filter, such as that disclosed in U.S. Pat. No. 10,881,371 to Helm et al. and U.S. Pat. No. 11,071,507 to Helm et al., all the above incorporated herein by reference. The imaging system 36 may also or alternatively be a C-arm, fluoroscope, computed tomography scan (CT), mobile magnetic resonance imager (MRI), etc.

The imaging system 36, when, for example, including the O-Arm® imaging system, may include a mobile cart 60 that includes a controller and/or control system 64. The control system 64 may include a processor and/or processor system 66 (similar to the processor 56) and a memory 68 (e.g., a non-transitory memory). The memory 68 may include various instructions that are executed by the processor 66 to control the imaging system 36, including various portions of the imaging system 36.

The imaging system 36 may include further additional portions, such as an imaging gantry 70 in which is positioned a source unit (also referred to as a source assembly) 74 and a detector unit (also referred to as a detector assembly) 78. In various embodiments, the detector 78 alone and/or together with the source unit may be referred to as an imaging head of the imaging system 36. The gantry 70 is moveably connected to the mobile cart 60. The gantry 70 may be O-shaped or toroid shaped, wherein the gantry 70 is substantially annular and includes walls that form a volume in which the source unit 74 and detector 78 may move. The mobile cart 60 may also be moved. In various embodiments, the gantry 70 and/or the cart 60 may be moved while image data is acquired, including both being moved simultaneously. Also, the imaging system 36 via the mobile cart 60 can be moved from one operating theater to another (e.g., another room). The gantry 70 can move relative to the cart 60, as discussed further herein. This allows the imaging system 36 to be mobile and moveable relative to the subject 28, thus allowing it to be used in multiple locations and with multiple procedures without requiring a capital expenditure or space dedicated to a fixed imaging system.

The processor 66 may be a general-purpose processor or an application specific application processor. The memory system 68 may be a non-transitory memory such as a spinning disk or solid-state non-volatile memory. In various embodiments, the memory system may include instructions to be executed by the processor 66 to perform functions and determine results, as discussed herein.

In various embodiments, the imaging system 36 may include an imaging system that acquires images and/or image data by the use of emitting x-rays and detecting x-rays after interactions and/or attenuations of the x-rays with or by the subject 28. The x-ray imaging may be an imaging modality. It is understood that other imaging modalities are possible, such as other high energy beams, etc.

Figure 2:
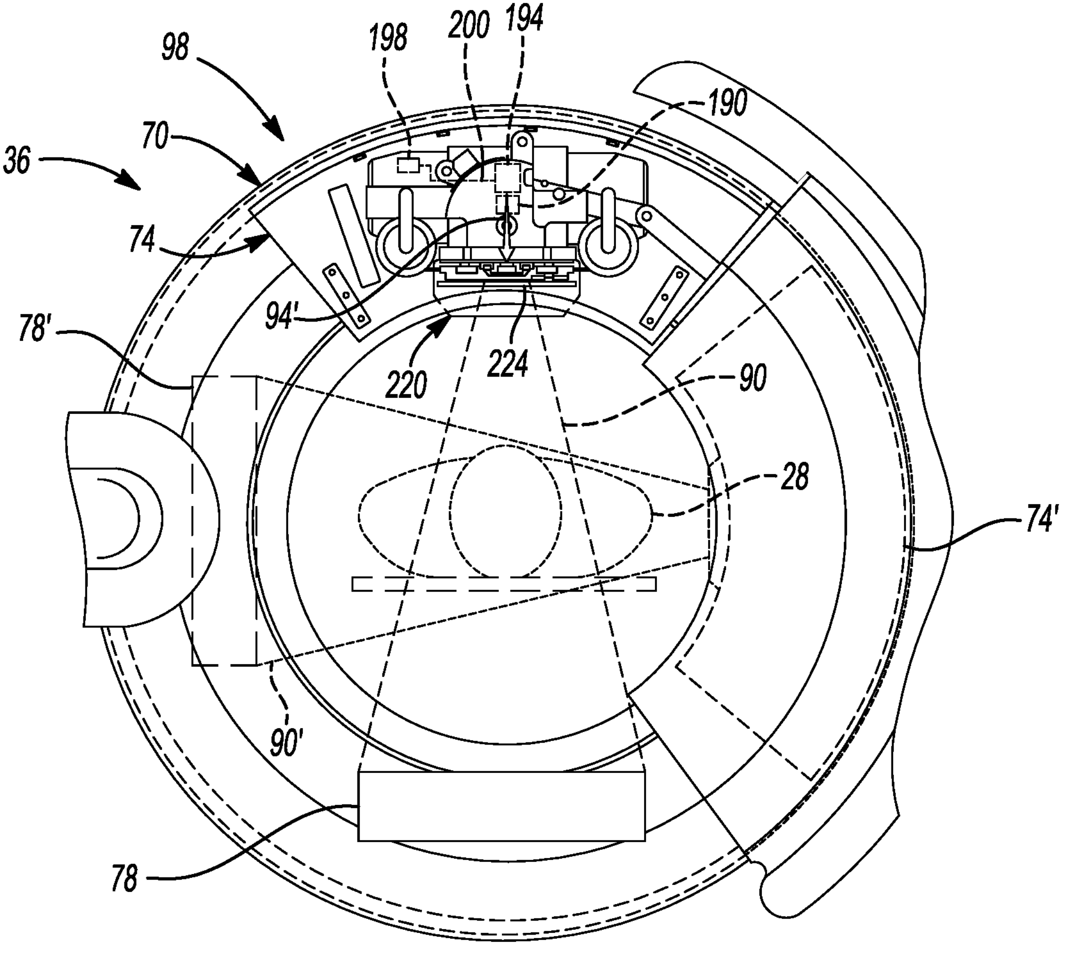
FIG. 2 is a detailed schematic view of an imaging system with a source and detector configured to move around a subject, according to various embodiments.

Thus, in the imaging system 36, the source unit 74 may be an x-ray emitter that can emit x-rays at and/or through the patient 28 to be detected by the detector 78. As is understood by one skilled in the art, the x-rays emitted by the source 74 can be emitted in a cone 90 along a selected main vector 94 and detected by the detector 78, as illustrated in FIG. 2. The source 74 and the detector 78 may also be referred to together as a source/detector unit 98, especially wherein the source 74 is generally diametrically opposed (e.g., 180 degrees (°) apart) from the detector 78 within the gantry 70.

The imaging system 36 may move, as a whole or in part, relative to the subject 28. For example, the source 74 and the detector 78 can move around the patient 28, e.g., a 360° motion, spiral, portion of a circle, etc. The movement of the source/detector unit 98 within the gantry 70 may allow the source 74 to remain generally 180° opposed (such as with a fixed inner gantry or rotor or moving system) to the detector 78. Thus, the detector 78 may be referred to as moving around (e.g., in a circle or spiral) the subject 28 and it is understood that the source 74 is remaining opposed thereto, unless disclosed otherwise.

Also, the gantry 70 can move isometrically (also referred as "wag") relative to the subject 28 generally in the direction of arrow 100 around an axis 102, such as through the cart 60, as illustrated in FIG. 1. The gantry 70 can also tilt relative to a long axis 106 of the patient 28 illustrated by arrows 110. In tilting, a plane of the gantry 70 may tilt or form a non-orthogonal angle with the axis 106 of the subject 28.

The gantry 70 may also move longitudinally in the direction of arrows 114 along the line 106 relative to the subject 28 and/or the cart 60. Also, the cart 60 may move to move the gantry 70. Further, the gantry 70 can move up and down generally in the direction of arrows 118 relative to the cart 30 and/or the subject 28, generally transverse to the axis 106 and parallel with the axis 102.

The movement of the imaging system 36, in whole or in part is to allow for positioning of the source/detector unit (SDU) 98 relative to the subject 28. The imaging device 36 can be precisely controlled to move the SDU 98 relative to the subject 28 to generate precise image data of the subject 28. The imaging device 36 can be connected to the processor 56 via a connection 120, which can include a wired or wireless connection or physical media transfer from the imaging system 36 to the processor 56. Thus, image data collected with the imaging system 36 can be transferred to the processing system 56 for navigation, display, reconstruction, etc.

The source 74, as discussed herein, may include one or more sources of x-rays for imaging the subject 28. In various embodiments, the source 74 may include a single source that may be powered by more than one power source to generate and/or emit x-rays at different energy characteristics. Further, more than one x-ray source may be the source 74 that may be powered to emit x-rays with differing energy characteristics at selected times.

According to various embodiments, the imaging system 36 can be used with an un-navigated or navigated procedure. In a navigated procedure, a localizer and/or digitizer, including either or both of an optical localizer 130 and/or an electromagnetic localizer 138 can be used to generate a field and/or receive and/or send a signal within a navigation domain relative to the subject 28. Other navigation modalities may also be used, such as ultrasound, sonar, etc. The navigated space or navigational domain relative to the subject 28 can be registered to the image 40. Correlation, as understood in the art, is to allow registration due to determination a translation map of a navigation space defined within the navigational domain and an image space defined by the image 40. A patient tracker or dynamic reference frame 140 can be connected to the subject 28 to allow for a dynamic registration and maintenance of registration of the subject 28 to the image 40.

In various embodiments, the imaging system 36 can generate image data that may be used to generate, such as by reconstruction, the image 40 and define an image space that can be registered to a patient space or navigation space that is defined by and/or relative to the patient 28. In various embodiments, the position of the patient 28 relative to the imaging system 36 can be determined by a navigation system, which may incorporate one or more of the localizers, with the patient tracking device 140 and the imaging system tracking device(s) 174 to assist in and/or maintain registration. Accordingly, the position of the patient 28 relative to the imaging system 36 can be determined.

Manual or automatic registration of the image space to the subject space can occur. In various embodiments, the registration can occur by matching fiducial points in image data with fiducial points on the patient 28. The fiducial points may be anatomical and/or artificial. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in U.S. patent application Ser. No. 12/400,273, filed on Mar. 9, 2009, now published as U.S. Pat. App. Pub. No. 2010/0228117; in U.S. Pat. No. 9,737,235, issued Aug. 22, 2017, U.S. Pat. No. 8,238,631, all incorporated herein by reference.

According to various embodiments, the imaging system 36 can be used with an un-navigated or navigated procedure. In a navigated procedure, a localizer and/or digitizer, including either or both of the optical localizer 130 and/or an electromagnetic localizer 138 can be used to generate a field and/or receive and/or send a signal within a navigation domain relative to the patient 28. The navigated space or navigational domain relative to the patient 28 can be registered to the image 40. Correlation, as understood in the art, is to allow registration of a navigation space defined within the navigational domain and an image space defined by the image 40. The patient tracker or dynamic reference frame 140 can be connected to the patient 28 to allow for a dynamic registration and maintenance of registration of the patient 28 to the image 40.

Once registered, the navigation system with or including the imaging system 36, can be used when and/or to perform selected procedures. Selected procedures can use the image data generated or acquired with the imaging system 36. Further, the imaging system 36 can be used to acquire image data at different times relative to a procedure. As discussed herein, image data can be acquired of the patient 28 prior to the procedure for collection of automatically registered image data or cine loop image data. Also, the imaging system 36 can be used to acquire images for confirmation of a portion of the procedure. Thus, image data may be acquired at any appropriate time and may be registered to the patient 28.

Upon registration and tracking of the instrument 144, a graphic representation 180 (e.g., an icon, indicium, animation or other or visual representation) may be displayed relative to, including overlaid (e.g., superimposed) on, the image 40. The image 40 may be an appropriate image and may include one or more 2D images, such as 2D images that are acquired at different planes. Images may also be a 3D image, or any appropriate image as discussed herein.

The patient tracking device or dynamic registration device 140 and an instrument 144 can then be tracked relative to the subject 28 to allow for a navigated procedure. The instrument 144 can include a tracking device, such as an optical tracking device 148 and/or an electromagnetic tracking device 152 to allow for tracking of the instrument 144 with either or both of the optical localizer 130 or the electromagnetic localizer 138. A navigation/probe interface device 158 may have communications (e.g., wired or wireless) with the instrument 144 (e.g., via a communication line 156), with the electromagnetic localizer 138 (e.g., via a communication line 162), and/or the optical localizer 130 (e.g., via a communication line 166). The interface 158 can also communicate with the processor 56 with a communication line 168 and may communicate information (e.g., signals) regarding the various items connected to the interface 158. It will be understood that any of the communication lines can be wired, wireless, physical media transmission or movement, or any other appropriate communication. Nevertheless, the appropriate communication systems can be provided with the respective localizers to allow for tracking of the instrument 144 relative to the subject 28 to allow for illustration of a tracked location of the instrument 144 relative to the image 40 for performing a procedure.

One skilled in the art will understand that the instrument 144 may be any appropriate instrument, such as a ventricular or vascular stent, spinal implant, neurological stent or stimulator, ablation device, or the like. The instrument 144 can be an interventional instrument or can include or be an implantable device. Tracking the instrument 144 allows for viewing a location (including x, y, z position and orientation) of the instrument 144 relative to the subject 28 with use of the registered image 40 without direct viewing of the instrument 144 within the subject 28.

Further, the imaging system 36, such as the gantry 70, can include an optical tracking device 174 and/or an electromagnetic tracking device 178 to be tracked with the respective optical localizer 130 and/or electromagnetic localizer 138. Accordingly, the imaging device 36 can be tracked relative to the subject 28 as can the instrument 144 to allow for initial registration, automatic registration, or continued registration of the subject 28 relative to the image 40. Registration and navigated procedures are discussed in the above incorporated U.S. Pat. No. 8,238,631, incorporated herein by reference. Upon registration and tracking of the instrument 144, an icon 180 may be displayed relative to, including overlaid on, the image 40. The image 40 may be an appropriate image and may include a long film image, 2D image, 3D image, or any appropriate image as discussed herein.

With continuing reference to FIG. 2, according to various embodiments, the source 74 can include a single assembly that may include a single x-ray tube 190 that can be connected to a switch 194 that can interconnect a first power source 198 via a connection or power line 200. As discussed above, x-rays can be emitted from the x-ray tube 190 generally in the cone shape 90 towards the detector 78 and generally in the direction from the x-ray tube 190 as indicated by arrow, beam arrow, beam or vector 94. The switch 194 can switch power on or off to the tube 190 to emit x-rays of selected characteristics, as is understood by one skilled in the art. The vector 94 may be a central vector or ray within the cone 90 of x-rays. An x-ray beam may be emitted as the cone 90 or other appropriate geometry. The vector 94 may include a selected line or axis relevant for further interaction with the beam, such as with a filter member, as discussed further herein.

The subject 28 can be positioned within the x-ray cone 90 to allow for acquiring image data of the subject 28 based upon the emission of x-rays in the direction of vector 94 towards the detector 78. The x-ray tube 190 may be used to generate two-dimensional (2D) x-ray projections of the subject 28, including selected portions of the subject 28, or any area, region or volume of interest, in light of the x-rays impinging upon or being detected on a 2D or flat panel detector, as the detector 78. The 2D x-ray projections can be reconstructed, as discussed herein, to generate and/or display three-dimensional (3D) volumetric models of the subject 28, selected portion of the subject 28, or any area, region or volume of interest. As discussed herein, the 2D x-ray projections can be image data acquired with the imaging system 36, while the 3D volumetric models can be generated or model image data.

For reconstructing or forming the 3D volumetric image, appropriate techniques include Expectation maximization (EM), Ordered Subsets EM (OS-EM), Simultaneous Algebraic Reconstruction Technique (SART) and Total Variation Minimization (TVM), as generally understood by those skilled in the art. Various reconstruction techniques may also and alternatively include machine learning systems and algebraic techniques. The application to perform a 3D volumetric reconstruction based on the 2D projections allows for efficient and complete volumetric reconstruction. Generally, an algebraic technique can include an iterative process to perform a reconstruction of the subject 28 for display as the image 40. For example, a pure or theoretical image data projection, such as those based on or generated from an atlas or stylized model of a "theoretical" patient, can be iteratively changed until the theoretical projection images match the acquired 2D projection image data of the subject 28. Then, the stylized model can be appropriately altered as the 3D volumetric reconstruction model of the acquired 2D projection image data of the selected subject 28 and can be used in a surgical intervention, such as navigation, diagnosis, or planning. The theoretical model can be associated with theoretical image data to construct the theoretical model. In this way, the model or the image data 40 can be built based upon image data acquired of the subject 28 with the imaging device 36.

With continuing reference to FIG. 2, the source 74 may include various elements or features that may be moved relative to the x-ray tube 190. In various embodiments, for example, a collimator 220 may be positioned relative to the x-ray tube 190 to assist in forming the cone 90 relative to the subject 28. The collimator 220 may include various features such as movable members that may assist in positioning one or more filters within the cone 90 of the x-rays prior to reaching the subject 28. One or more movement systems 224 may be provided to move all and/or various portions of the collimator 220. Further, as discussed further herein, various filters may be used to shape the x-ray beam, such as shaping the cone 90, into a selected shape prior to reaching the subject 28. In various embodiments, as discussed herein, the x-rays may be formed into a thin fan or plane to reach and pass through the subject 28 and be detected by the detector 78. Accordingly, the source 74 including the collimator 220 may include a filter assembly, such as that disclosed in U.S. Pat. No. 10,881,371 to Helm et al., incorporated herein by reference.

As discussed above, image data may be acquired of the subject. The image data may be processed and/or analyzed for various purposes, such as identifying implants to be positioned in the subject. As discussed above various procedures may occur to the subject 28. In various embodiments, for example, a spinal fusion may be a procedure that includes an implant that may include, among other items, a fixation member, rod, or plate that is connected to one or more vertebrae. The rod may be designed to assist in providing a treatment to the subject 28. For example, a spinal implant may include an implant such as one or more included with a CD Horizon®, Solara®, Voyager®, Zevo®, Catalyft®, and Infinity® implant members (e.g., spinal implants) and/or systems, including fixation portions, all sold by Medtronic, Inc. having a place of business in Minnesota, USA. Further, a patient specific rod may be designed based upon information acquired regarding the subject 28 to assist in planning and determining the implant.

Figure 3:
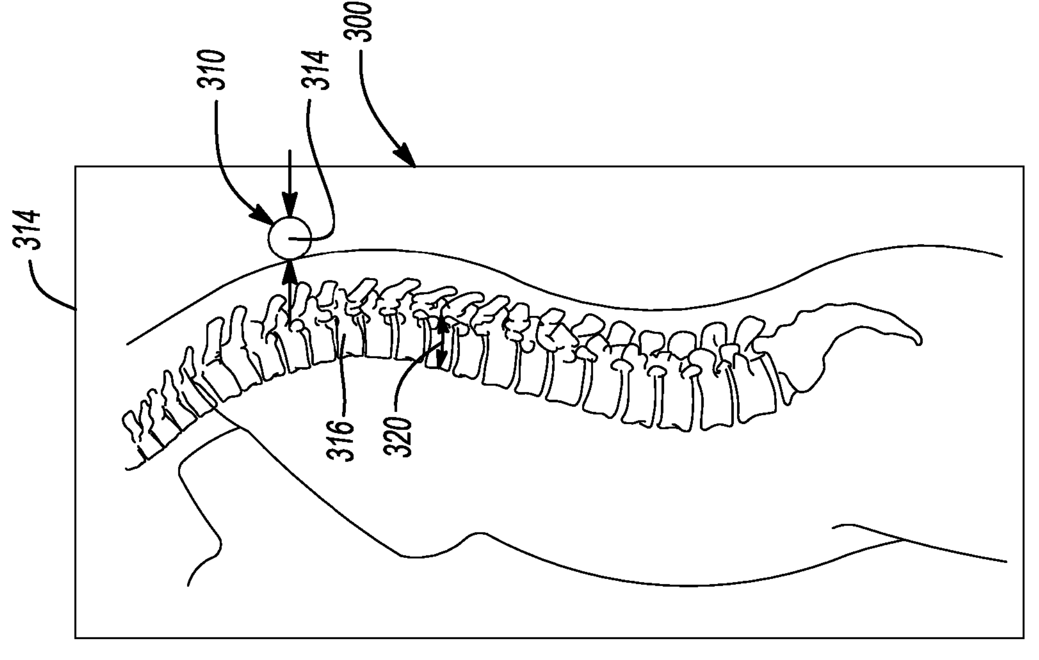
FIG. 3 is an image of a subject.

With continuing reference to FIGS. 1 and 2, and additional reference to FIG. 3, image data may be acquired of the subject 28. In various embodiments, for example, a two-dimensional x-ray projection 300 may be acquired of the subject 28. It is understood that the x-ray projection may be acquired with the imaging system 36, or any appropriate imaging system. In various embodiments, the x-ray projection 300 may be a standing x-ray of the subject 28. It is understood that other appropriate image data may be of the subject 28, and the x-ray images are merely exemplary. Further, it is understood that implants procedures may occur relative to the subject 28 and a spinal rod implant is merely exemplary. Further, in various embodiments a first image data may be used for planning a procedure for the subject 28.

Regardless, the image data 300 of the subject may be displayed on the display device and/or evaluated or manipulated substantially automatically. For example, a processor, such as the processor modules noted above, may evaluate to the x-ray or other image data to calibrate the image data. In various embodiments, for example, a calibration module or portion 310 may be included in the image data. For example, the calibration module 310 may include a sphere that has a known dimension or geometry. For example, the calibration module 310 as a sphere may include a diameter 314 that is known. The diameter 314 may be in any appropriate diameter, such as 1 centimeter (cm), 1 millimeter (mm), 5 cm, or any appropriate dimension. It is further understood that the calibration module or member 310 need not be a sphere, but can include any appropriate geometry.

Regardless, the calibration module 310 may have a known geometry and/or size that may be used to calibrate the image 300. For example, the image 300 may include one or more vertebrae 316. The vertebrae 316 may be imaged in the image 300 and be displayed and/or analyzed. Based upon the known calibration module 310, including its geometry or size 314, the size or geometry of the vertebrae 316 may be known. For example, the image of the calibration module 310 may be analyzed relative to the vertebrae 316 to determine a dimension of the vertebrae 316 based upon the known geometry and/or size, such as the diameter 314, of the calibration module 310. Therefore, a size and geometry of the vertebrae may be known to have a dimension 320 that is some portion of the dimension of the calibration module 310. For example, the dimension 320 may be substantially equal to the diameter 314 of the calibration module 310. Therefore, the dimension 320 of the vertebrae may be known to be equal to the dimension of the calibration module 310. Other appropriate analysis may include determining the number of pixels that define the diameter 314 of the calibration module 310 and thereby determining a value or dimension of the pixel in the image data 300. A direct correlation, such as a size of the calibration model 310 in the image 300 directed to any other appropriate portion, such as the vertebrae 316, may also be used. Additionally, calibration can occur by referencing vertebra dimensions on multiple imaging modalities (e.g., X-ray and CT) or be taken directly from a single modality image with embedded calibration functionality (e.g., Multitom Rax® medical imaging system sold by Siemens Healthcare GmbH or EOS Edge® medical imaging system sold by EOS IMAGING). That is, dimensions of various members that occur in a first image data may be used to calibrate other, e.g., a second, image data relative thereto.

Once the image data 300 is calibrated, selected portions of the image data, including all of the image data and/or a region of interest in the image 300, may be calibrated such that dimensions within the image data 300 may be known. For example, a determination of the size of the vertebrae 316 may be made, a distance between the vertebrae 316, the position of vertebrae relative to one another, and other dimensions. Therefore, the image data 300 may become calibrated image data 330, as illustrated in FIG. 4.

The calibrated image 330 may be used for various purposes, such as planning a procedure. For an implanting procedure, a selected position of one or more of the vertebrae 316 may be selected. For example, a first vertebrae **316*a* may be selected to be moved a selected distance or position relative to a second vertebrae 316*b*. In the calibrated image 330, the planned movement of the two vertebrae 316*a*, 316*b* relative to one another may cause a wedge or opening 342 to be formed and be visible in the calibrated image 330 during or after planning. It is understood that the planning of the procedure may be performed for any number of selected vertebrae and the two vertebrae 316*a*, 316*b* is merely exemplary. Further planned positions of a screw, such as a first screw 344 may be made. In addition, a rod or fixation member 350 may also be selected or planned. The rod 350 may be positioned or planned relative to the calibrated image 330 to assist in holding or moving the vertebrae to the selected positions, such as the positions of the vertebrae 316*a*, 316*b***.

In the calibrated image 330, the planned position of the rod 350, the selected vertebrae, and fixation members, such as the fixation screw 344, may be planned. For example, the user 24 may manually manipulate various portions of the calibrated image 330 to position the vertebrae or portions thereof. In addition, or alternatively thereto, various planning or support systems may be provided. For example, the Mazor X Stealth Edition® computer and software system alone and/or in combination with the Mazor X robotic and guide systems, may be used to assist in the planning, both sold by Medtronic, Inc. For example, the selected processing modules, including those discussed above and/or included with Mazor X Stealth Edition® computer and software system, may analyze the calibrated image 330 and a selected in positioning of various vertebrae, fixation points, and the rod 350. Thus, the calibrated image 330 and the related planning procedure may be performed and/or augmented with the automatic systems, such as by executing instructions with the processor module.

Figure 4:
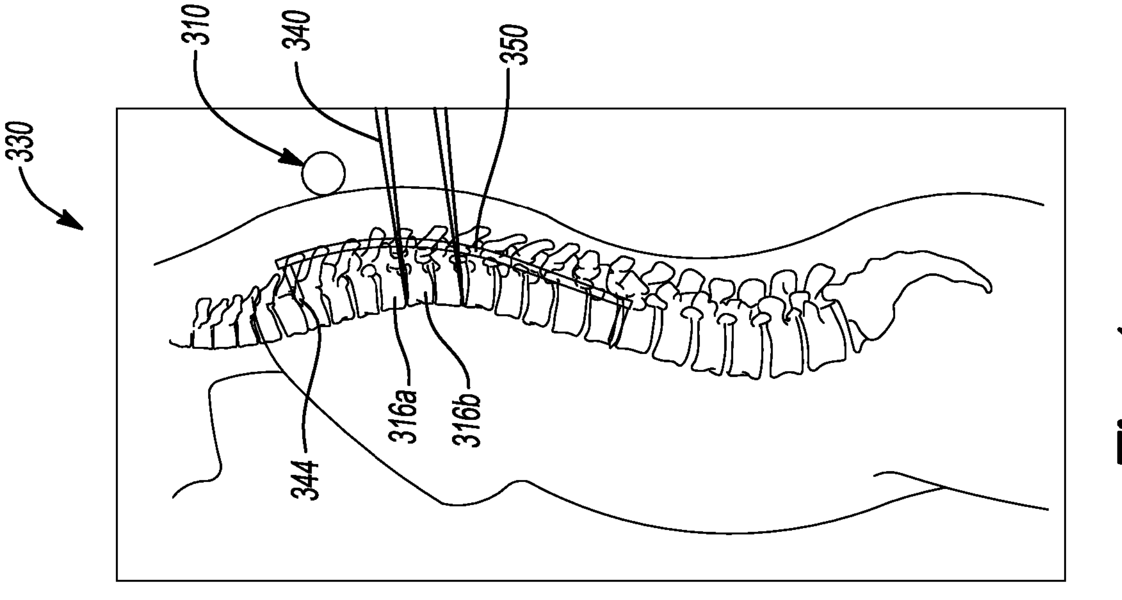
FIG. 4 is an image of the subject that is calibrated and includes a portion of a plan.
Figures 5, 6:
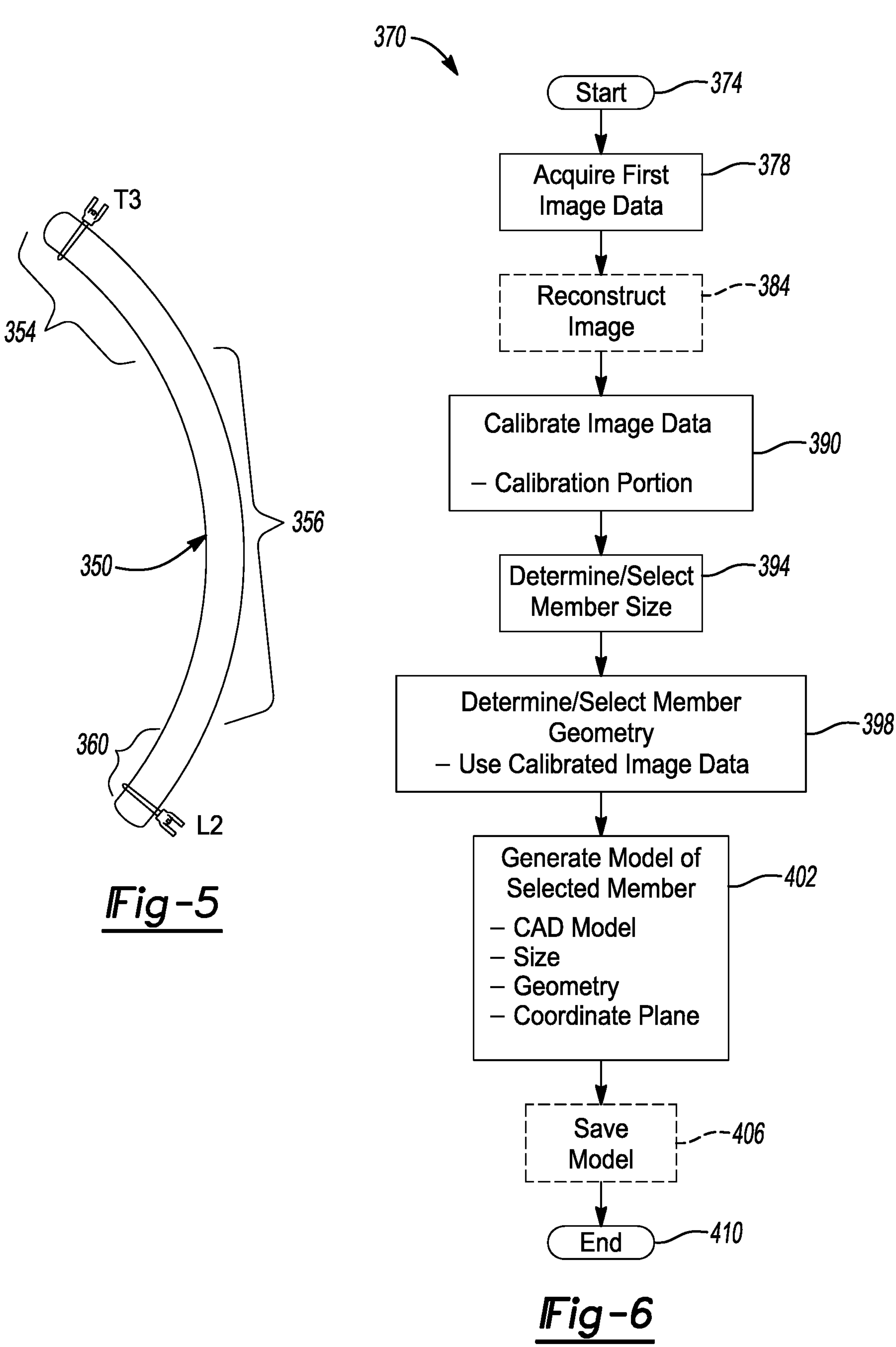
FIG. 5 is a digital graphical illustration of a model of an implant.
FIG. 6 is a flow chart of a process for generating a model, according to various embodiments.

Regardless, the calibrated image 330, is illustrated in FIG. 4 and may be used to plan or determine a geometry of the rod 350. Turning reference to FIG. 5, therefore, a model may be formed of the rod 350. The rod 350 illustrated in FIG. 4 and FIG. 5 may be a model of a physical rod. The model 350 may include various features of the product, such as a selected size (e.g., length and cross-sectional dimension), geometry (e.g., curves), and the like. For example, the model 350 may include a selected geometry that may include a first section 354 having a first length and curve, a second section 356 having a second length and curve, and a third section 360 having a third a length and curve. For example, the rod may include a circular cross-action, and oval cross-section, and angular or public valve cross-section, or any appropriate geometry.

The geometry of the rod model 350 may include any appropriate three-dimensional geometry. Therefore, the rod model 350 may include curves that are both medial and lateral relative to the subject 28, inferior and superior relative to the subject 28, and anterior and posterior relative to the subject 28. Nevertheless, the rod model 350 may be developed to achieve the geometry of the subject generated within the calibrated image 330. The rod model 350, therefore, may include the appropriate geometry and features based upon the planning is illustrated relative to FIGS. 4 and 5.

Turning reference to FIG. 6, a process 370 is illustrated. The process 370 may illustrate to the portions to generate to the broad model 350 as illustrated in FIG. 5. The process 370 may begin in Start block 374 and include acquiring a first image data in block 378. Acquiring the first image data may include the uncalibrated image data 300, as illustrated in FIG. 3. The image data may be of the subject 28 and may be acquired in any appropriate manner. For example, as discussed above, the image data 300 may include one or more two-dimensional projections of the subject 28. Image data may be acquired with an appropriate imaging system, such as x-ray imaging system, an MRI imaging system, or the like.

The image data may be optionally reconstructed to generate an image in block 384, as illustrated in FIG. 3. Reconstructing the image in block 384 may include generating an image based upon the image data acquired with a selected imaging system. For example, as discussed above, the imaging system 36 may include the O-Arm® imaging system that may acquire a plurality of projections of the subject 28. For example, to achieve an image that includes an entire spine of the subject 28, the gantry may move in the direction of the arrow 110. The various projections may, therefore, be stitched together to achieve the image. Thus, the reconstruction of the image in block 384 may be used to generate an appropriate image, generated image to be viewed, or the like.

The image data may then be calibrated in block 390. As discussed above the calibration of the image data may include evaluating the image data relative to a calibration member, such as the calibration member 310. The calibration may include the evaluation of the image data based upon the known geometry and size of the calibration member 310. Thus, each portion of the image 300 may have a known size and/or geometry based upon the calibration member 310

Using the calibrated image data, a determination or selection of a member size may be made in block 394. The member may be, for example, an implant including the rod disclosed above. A size of the member may include a length of a rod, such as the rod modeled as the model 350. The size may further include a cross sectional size, an overall length, a segmented length, or any other appropriate size. A segmented length may include a length or size between various portions of the rod that may differ in geometry, such as an angle or change and angles.

A geometry of the member may be selected to be determined in block 398, also based upon the calibrated image data. The geometry may include an angle, number of angles, distance between angles, geometry and three-dimensional space relative to the calibrated image 330, and other appropriate geometric configurations.

Based upon the determined size and geometry, from blocks 394 and 398, the model 350 may be generated in block 402. The generated model may be any appropriate model, such as a computer aided design (CAD) model. The model may be a digital format model that may be used for various purposes, as discussed herein. The model may include a graphical representation of a rod that may be made or produced for the subject 28 to be used by the user 24 during a procedure. The model 350 may, therefore, include the determined size and geometry. The rod may also define a coordinate plane or coordinate space that may be displayed relative to an image of the subject, such as the calibrated image 330. In various embodiments, as discussed herein, the model 350 that may be displayed is superimposed on the calibrated image 330, or any appropriate image. The model 350 can be of any selected spinal implant and may be overlayed (i.e., superimposed) within the image based on reference anatomy or a pre-operative surgical plan.

The model may then be saved in block 406. Saving the model in block 406 is optional but may be used for allowing the generated model to be saved for a later purpose. It is understood, however, saving the model in block 406 is optional and the model may simply be used substantially instantaneously for a selected purpose, such as that discussed herein. Therefore, the process to generate the model 370 may End in block 410. The generation of the model, such as the rod model 350, may be used to assist in planning and/or validating a procedure as discussed herein.

Figure 7:
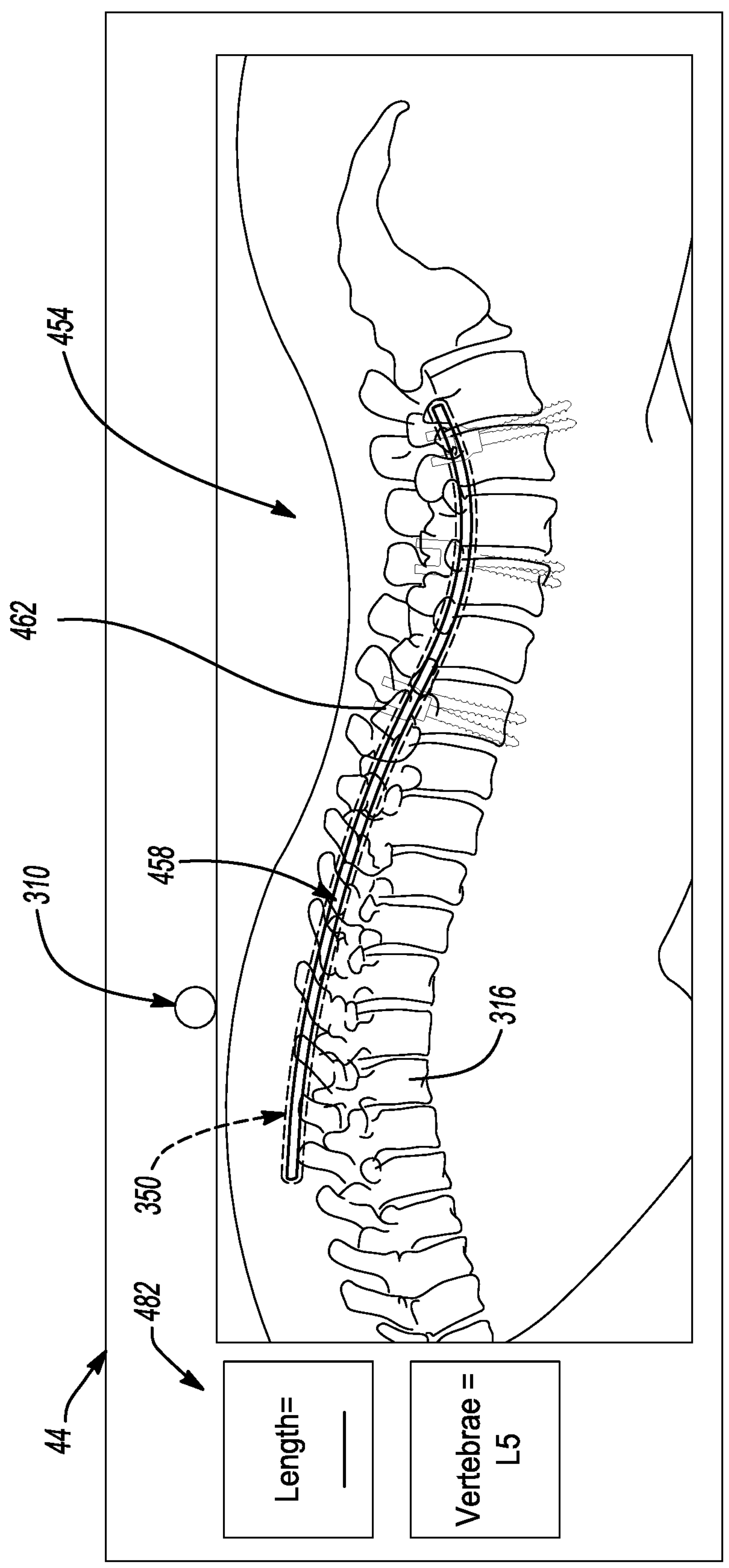
FIG. 7 is an illustration of a graphical representation of a model superimposed on an image of a subject, according to various embodiments.
Figure 8:
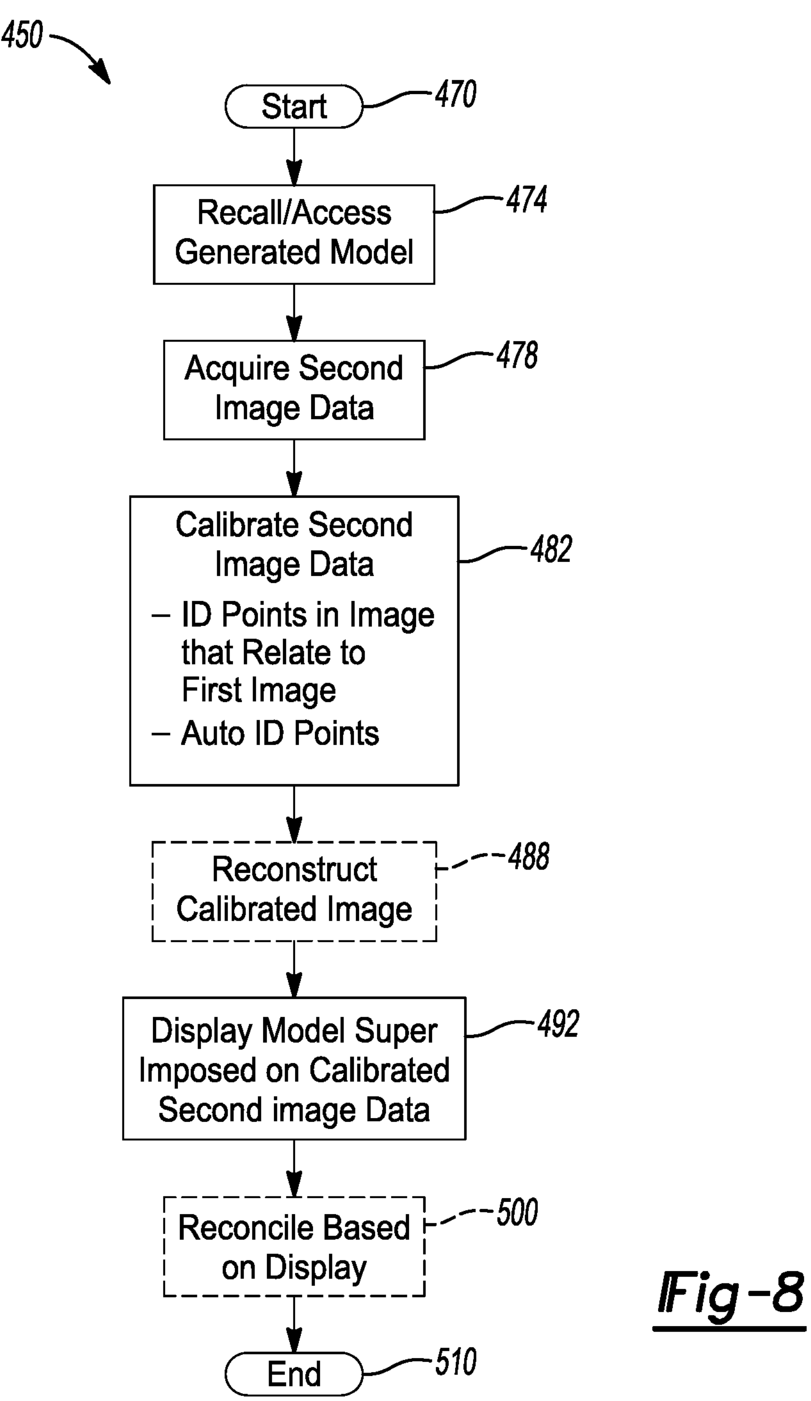
FIG. 8 is a flowchart of a reconciliation process, according to various embodiments.

Turning reference to FIGS. 7 and 8, the model 350 may be used in a reconciliation or validation process 450 is illustrated in FIG. 8. The validation or reconciliation process may include displaying the rod model 350, as a graphical representation of the rod, superimposed on a second image 454 of the subject. The second image 454 may be after implantation of a rod 458 that is fixed in the subject with one or more of the fixation members, such as screws 462. The rod 458 may be imaged in the second image 454 of the subject 28, such as with the imaging system 36. For example, the image data may be acquired with an x-ray imaging system and the rod 458 may be a radiopaque member. Therefore, the rod 458 would appear in the image data 454 of the subject 28. The validation or reconciliation process may include displaying of the model 350 superimposed on the image of the rod 458 in the subject to confirm placement of the rod 458 in the subject in a selected or planned position.

The reconciliation process 450 may, therefore, begin block 470. The process may include a superimposing on a display device a graphical representation, such as based on the rod model 350, on the rod image 458. The process 450 may include recalling or accessing the generated model in block 474. As discussed above, the generated model may be saved in block 406. However, the model may be recalled or accessed in block 474. Recalling or accessing the model may include recalling it from a memory, recalling it directly from the planning processor module, or other appropriate access. Regardless the model may be called for various purposes, as discussed herein. As also discussed above, the model may include specific features of the rod 458. The features the rod may be used to generate the rod 458 to be implanted into the subject 28. The model 350, when recalled, may be used to generate an image that is displayed relative to an image of the subject 28, as discussed herein.

After planning the model 350, the model 350 may be used to create a rod, such as in a manufacturing process, including the geometry, size, and like for the subject 28. The rod may then be implanted at a certain time and the rod may be imaged in the subject 28 to acquire a second image data in block 478. The second image data acquired in block 478 may be the image data 454 and may be displayed, as illustrated in FIG. 7. The image data 454 may be displayed on the display device 44. The display device may also display various in The acquired second image data may be acquired of the subject 28 after a portion of the procedure, such as positioning of the rod 458 in the subject. The second image data may be acquired at any appropriate time, however, such as after a test placement of the rod, the fixation of a single one of the fixation members, or temporarily placing the rod on the subject 28.

The second image data may, however, be calibrated to the first image data in block 482. Calibrating the second image stated to the first image data may occur according to various techniques, such as including the calibration member 310 in the image acquired in block 478. The calibration member 310 may be positioned relative to the subject 28 for acquisition of the second image data. Thus, the calibration member 310 may be used to calibrate to the second image data of the subject.

The calibration member 310, being the same for the acquisition of the first image data and the second image data, therefore, calibration between the first and second image data may be ensured. In addition or alternatively thereto, the image data may be calibrated to one another such as selecting portions that are identical in each image data. For example, the vertebrae of 316*a* may be identified in the calibrated image 330 and in the image data 454. The vertebrae 316*a* may be identified by the user 24 in both image data. The selection of the vertebrae 316*a* may also or alternatively be automatic, such as by segmenting and/or identifying a geometry boundary of the vertebrae 316*a*. It is understood, however, that a determination of the geometry of the selected portion, such as the vertebrae 316*a*, may be used to allow the processor module to substantially automatically segment the vertebrae 316. The segmentation of the same portion, such as the vertebra 316*a*, in the first and second image data may be used for the calibration of the second image data in block 482. As discussed above, calibration may be performed according to a selected manner to achieve the determination of the appropriate size and geometry.

The second image data may be acquired in block 478 and may be calibrated to the first image data in block 482. An image may then be reconstructed with the calibrated image data in block 488. The reconstruction of the calibrated image data may be used to generate an image for display, such as the second image data 454. The second image may, again, be based on a plurality of projections, such as acquired with the imaging system 36. Therefore, the image 454 may be reconstructed based upon this the image data that is calibrated relative to and/or calibrated to be exactly as the calibrated first image 330.

The reconstructed image may be displayed, such as on the display 44. Further, the model 350 may be displayed, such superimposed on the display of the calibrated image in block 492. As illustrated in FIG. 7, the model 350 may be displayed superimposed, such as overlaid, on the image of the implanted rod 458. The implanted rod image 458 may be based upon acquired image data of the subject 28 including the implant. The overlay of the model 350 may be displayed on the display device 44 as a graphical representation of the rod or other spinal implant or planned technique which may be based upon the generated model 350, as discussed above. As a model is used to generate to the rod 458, the model 350 should be able to substantially overlay the image rod 458. The display device 44 may, therefore, display the model 350 superimposed on the x-ray image of the rod 458. The model 350 may be substantially automatically overlaid and/or moved by the user 24 or any appropriate user annually to display the overlaid model 350 on the route image 458. Alternatively or additionally, the model 350 could represent a planned removal of bone or soft tissue that would change an anatomical shape such as that of one or more vertebra 316 and/or an orientation of two or more vertebrae relative to each other.

As the rod model 350 is generated with the calibrated image data 330 and the second image data 454 is calibrated to the same calibration, the rod model 350 is a true representation of the rod relative to the image 454 and should directly overlay the rod image 458 when aligned. When the rod model 350 substantially overlays the rod image 458, the procedure may be validated and/or reconciled to the plan. Reconciliation can occur by direct visualization of the overlay image or through the quantification of a variance between the coordinate plane of rod model 350 and the location of one or more vertebral bodies. A variance than a selected amount (e.g., 3 mm) or percentage such as more than 10% may be output. Therefore, the user 24 and/or the system, such as the processor module executing instructions to determine an amount of overlay, may be used to reconcile the procedure based upon the display in block 500. The reconciliation may be manual, automatic, or a combination of both. For example, the user may move the model 350 to overlay on the rod image 458. The processor module may then execute instructions to determine an amount of boundary match between the model 350 and the rod image 458. The amount of overlay may be determined only by the user 24, only by the processor module executing selected instructions, or as a combination of both.

The process 450 may then end in block 510. The process 450, therefore, may be used to reconcile the placement of the rod in the subject 28 that may be imaged as the rod image 458 in the second image 454. The rod model overlaid on the rod image 458 may allow for a validation or reconciliation of the planned procedure relative to the performed procedure. Thus, the user 24 may reconcile or confirm the procedure being performed relative to the plan.

The procedure on the subject 28, as discussed above, may be planned relative to selected image data. The image data may be two-dimensional image data and may include a plan that is substantially two-dimensional to identify a planned curve of a portion of the subject 28, such as the spine of the subject. In various embodiments, however, image data and a related planned may be made relative to three-dimensional image data.

Figures 9, 10:
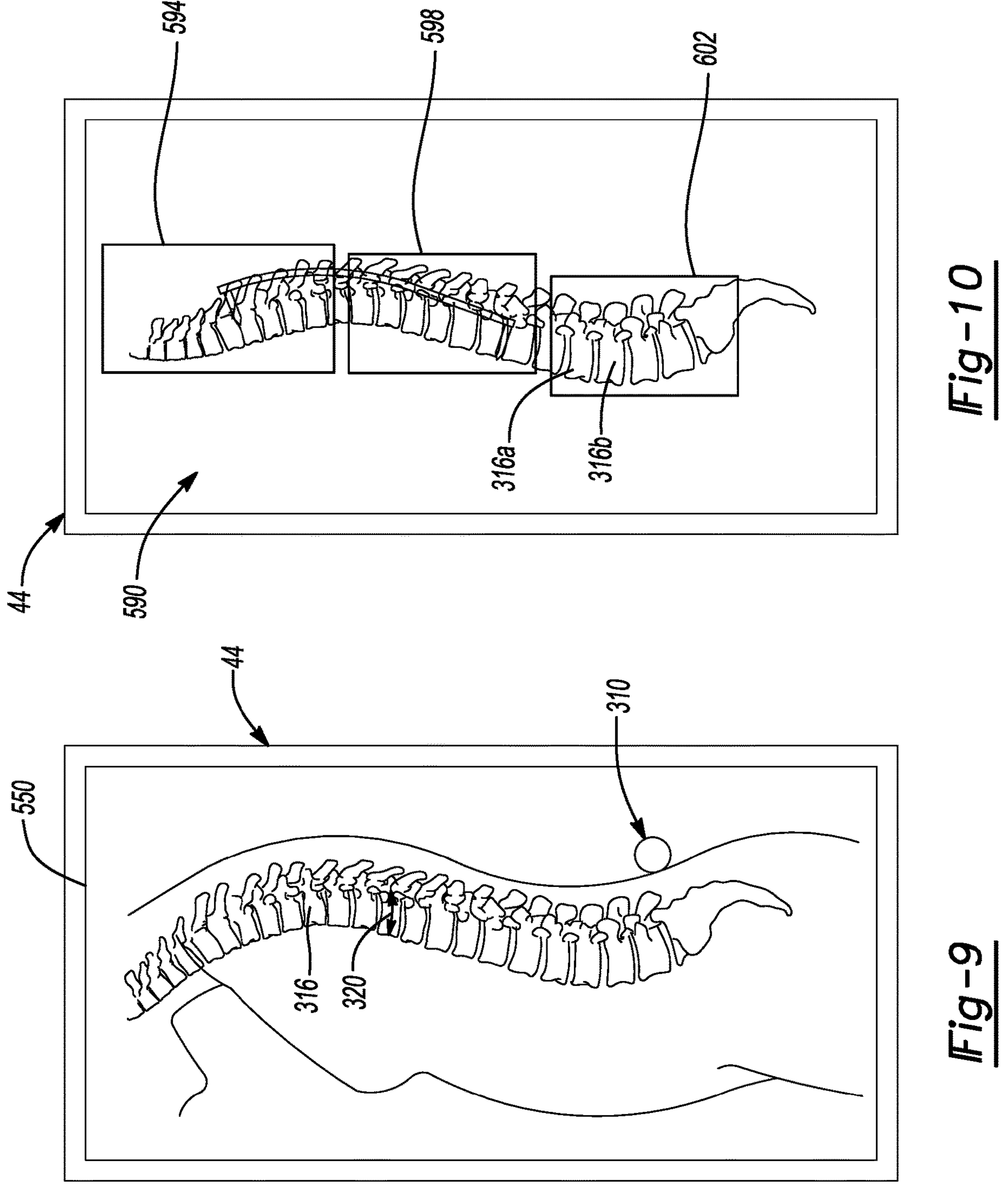
FIG. 9 is an image of a subject.
FIG. 10 is a 3D reconstruction of a subject.

With reference to FIG. 9 and FIG. 10, image data may be acquired of the subject 28 with an appropriate imaging system. For example, an image 550 may be generated with projections made or collected by the imaging system 36. As discussed above, the imaging system 36 may generate a plurality of projections of the subject 28 and a reconstruction may be made thereof, such as a 2D reconstruction and/or a 3D reconstruction. According to various embodiments, 2D images may also be registered to 3D images. Accordingly, a 3D image of the subject 28 may be acquired, such as a CT scan, and it may be registered to the image data acquired with a different or second imaging system. Regardless, the first image data 550 may be acquired of the subject.

Figure 12:
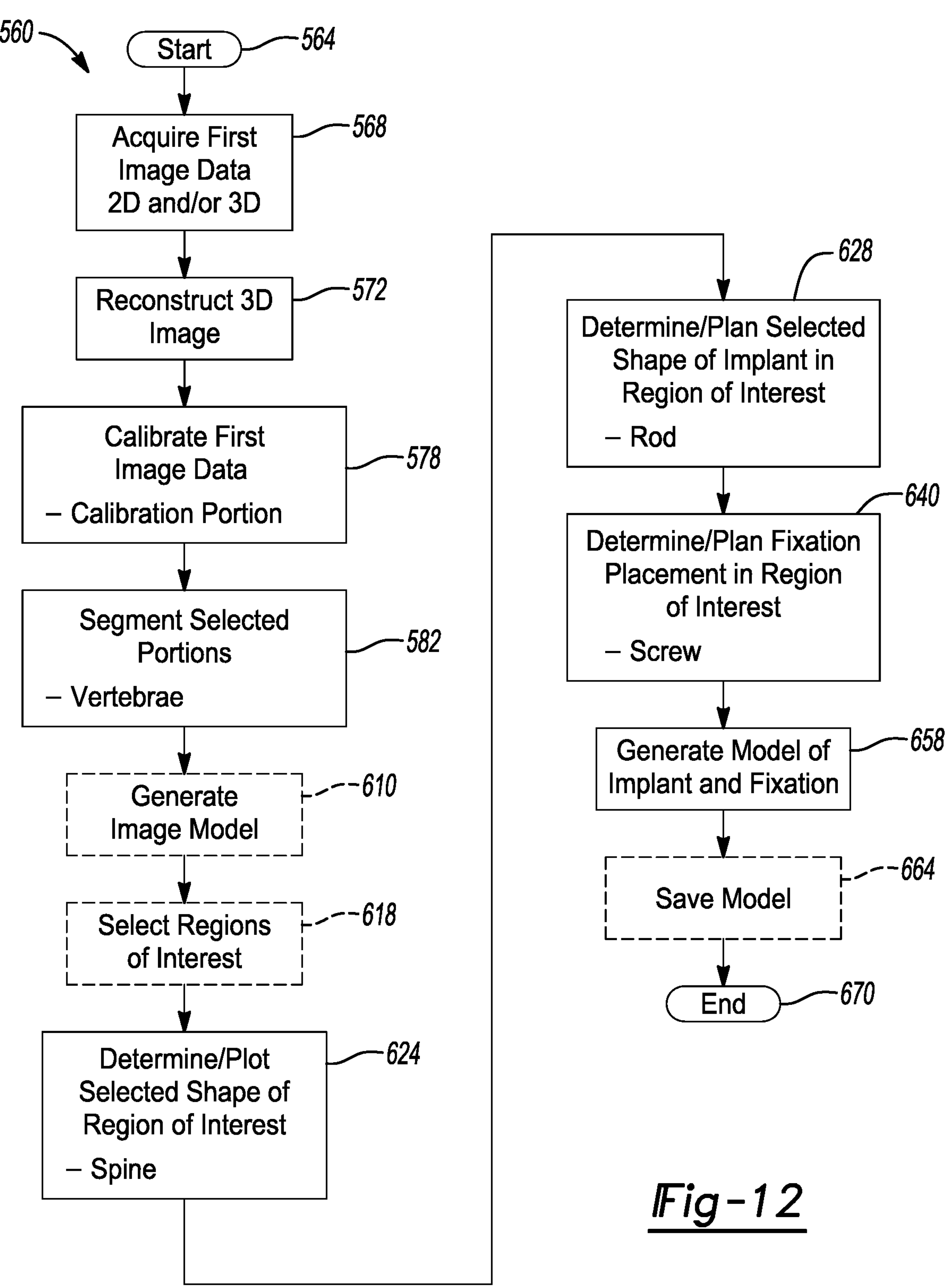
FIG. 12 is a flowchart of a process for generating a plan and a model, according to various embodiments.

With continuing reference to FIG. 9 and additional reference to FIG. 12, a plan may be generated of a procedure. The procedure plan may be a plan 560 that begins in Start block 564. Acquisition of first image data may then be made in block 568. The acquisition of the first image data may be made with the imaging system 36, as discussed above. Further the acquisition of the first image data may include in acquisition of 2D image data and an access or registration to three-dimensional image data. Regardless, the image data may be used to reconstruct a 3D image in block 572. With brief reference to FIG. 10, a 3D reconstruction may be made and/or displayed on the display device 44. The reconstruction may be based upon a plurality of image data acquired of the subject 28 and/or registration of different image data. Further, as discussed above, the imaging system 36 may acquire image data of the subject that is stitched together, such as to generate a long film view including image data that is not collected a single projection position. The long view may include, for example, an entire spine of the subject.

The image data may be calibrated in block 578. Returning reference to FIG. 9, as discussed above, the calibration member 310 may be included in the image data to allow for a calibration of the image data and/or the reconstruction. The calibration member 310 may be used to identify a size and geometry of various portions of the subject 28, such as the vertebrae 316. Therefore, the dimension 320 may be determined of the vertebrae 316 in a manner similar to that discussed above. Further a size and geometry of the subject or a selected region of interest, such as a spine or portion of the spine, may also be made.

The calibrated image data may then be segmented in block 582. With reference to FIG. 10, the display device 44 may display the 3D image data as a 3D image or model 590. The 3D model may be based entirely on the acquired image data and/or more fitting a standard atlas model of a selected subject, such as a human subject. Regardless of the process, however, the 3D image data 590 may be analyzed by the user 24 and/or the processor module, executing selected instructions, to plan a procedure. As discussed above, the processor module may execute instructions similar to those included in the Mazor X Stealth Edition® computer software and system sold by Medtronic, Inc. having a place of business in Minnesota, USA. The 3D image data may be segmented, such as to segment the vertebrae, in block 582. As illustrated in FIG. 10, the 3D image 590, for example displayed on the display device 44, may have a segmented vertebrae including the vertebrae 316*a*. Other vertebrae may also be segmented including the vertebrae 316*b*. It is understood, however, that any appropriate number of vertebrae may be segmented. Further regions or selected regions of interest may also be segmented as units, including a first region of interest 594, a second region of interest 598, and a third region of interest 602. It is understood that the three regions of interest are merely exemplary and not requirements. Thus, more or less regions of interest, if any are selected, may be selected.

Figure 11:
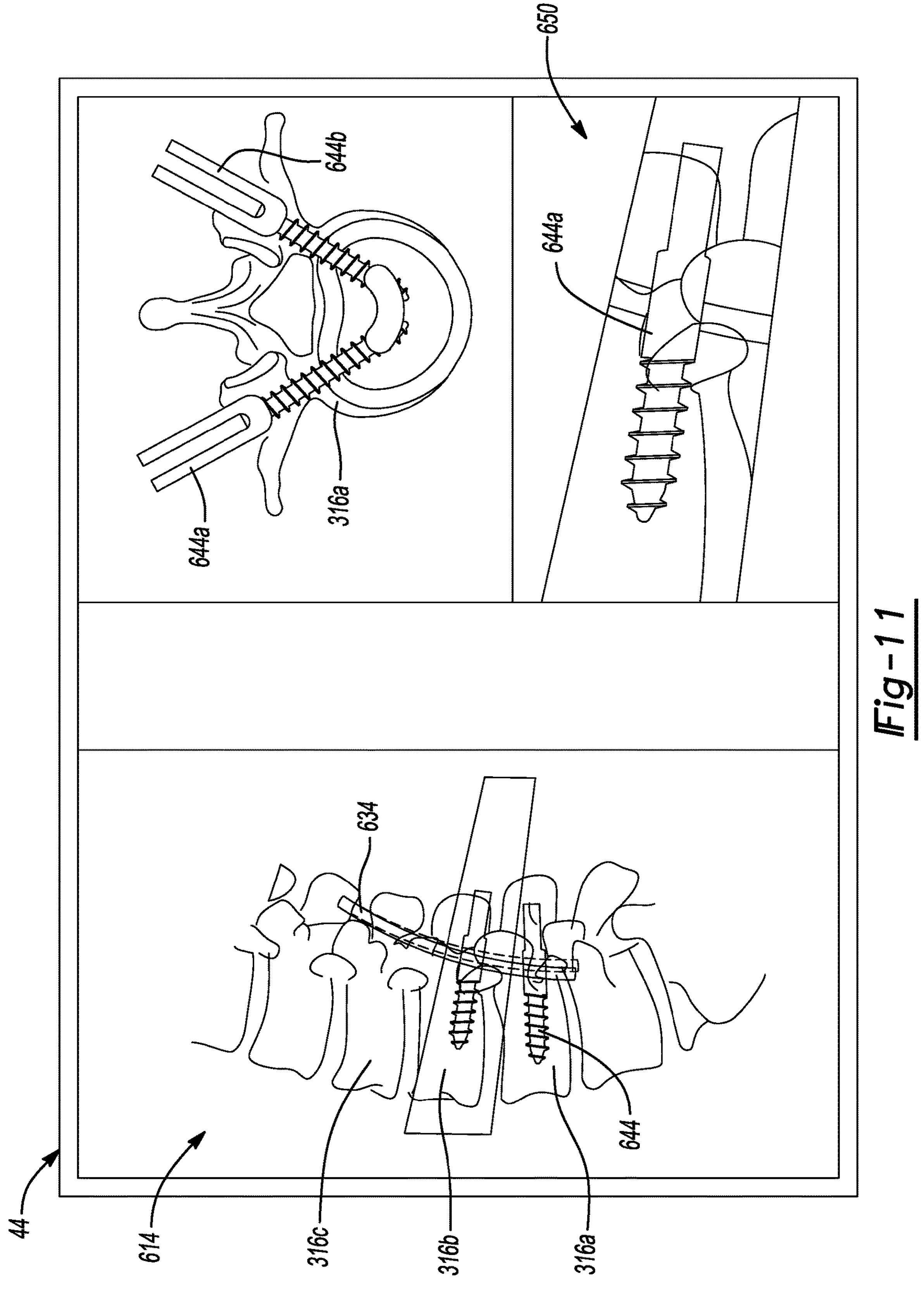
FIG. 11 is a graphical display of a plan for placement of implants after a procedure, according to various embodiments.

The segmented image data may also be used to generate a model in block 610. The generated image model is exemplary and not required, but may be used for various purposes, such as planning, as illustrated in FIG. 11. A model 614 may include the segmented portions or dimensions of the segment portions that are illustrated in displayed relative to one another to assist in planning. The regions of interest 594, 598, 602 may be selected at any appropriate time, such as with the generated model and/or in a three-dimensional data 590 in block 618. The selected regions may assist in defining a shape, procedure process, or the like for performing a procedure on the subject 28.

Once the image data is appropriately segmented and prepared, including pre-processing (e.g., the segmentation, identification selected regions, or the like) a plan may be determined. The pre-processing, however, may be carried out with a selected processor module that may include various segmentation techniques including edge detection by gradients, manual segmentation, such as by the user 24, or other appropriate pre-processing. The processing may allow for the image data to be appropriately analyzed for planning and generate the 3D image data and/or model of the subject 28. Nevertheless, is illustrated in FIG. 11, various planning portions may be reformed to assist in performing the procedure on the subject 28.

For example, a determined or planned selected shape of a region of interest may be made in block 624. As illustrated in FIG. 10, the spine of the subject 28 may be displayed and a shape thereof may be determined and/or planned to be achieved with a procedure (e.g., spinal implant and/or fusion). Further, or alternatively thereto, various regions of interest may be identified and shapes of each of the region of interest may also be determined or planned. Regardless of the technique, however, a shape of the spine may be determined and/or planned in block 624. The shape of the spine may assist and/or determine a shape of an implant, such as a rod in block 628. As illustrated in FIG. 11, the model 614 of the spine may include a rod model 634 which may be similar to the rod model 350 as discussed above. The rod model 634 may be designed or determined to achieve a shape of the spine that is determined in block 624. Further a model of each or a selected number of the vertebrae may be identified such as the first vertebrae 316*a* as L4, a second vertebrae 316*b* as L3, and a third vertebrae 316*c* as L2. Identification of the vertebrae may assist in forming the planning to achieve a selected shape of the spine and/or the implant, such as the rod in block 628.

A determination of fixation points or regions is made in block 640. The fixation regions may include positions of one or more screws, such as a planned position of the screw in L4. As illustrated in FIG. 11, a graphical representation of a screw 644 may be illustrated to have a selected orientation relative to the rod model 634 and at the vertebrae 316*a*. Further one or more additional fixation members may also be planned, as understood by one skilled in the art as illustrated in FIG. 11. For example, the L4 screw may include a plurality of screws including two screws that may be inserted bilaterally including the representations of screw 644*a* and 644*b*. Further additional details may include a in orientation, size, and the like. All of the information and plan may be displayed on the display device 44 and a further panel 650 included in the graphical representation of the screw 644*a*.

Therefore, a shape of the rod may be identified and generated as a rod model or implant model in block 658. The generated rod model may include a three-dimensional model of geometry, size, and the like. The rod model generated in block 658 may be for any one of the selected regions of interest and/or an entire portion of the spine. Accordingly, a plurality of rod models may be generated and/or a single rod model may be generated in block 658. The rod model may also include and/or have created in accordance therewith a model of the screws 644 and orientation and position relative to the vertebrae 316 of the subject. The model may be displayed on the display device 44 and/or superimposed on image data of the subject, such as the 3D image 590. The model may be displayed on the subject model 614, however, as illustrated in FIG. 11.

The model may be than saved in block 664, according to various embodiments. Saving of a model may allow it to be recalled at a selected time to assist in procedure, such as a reconciliation of a procedure. The saving of the model, however, is not required as discussed above. The procedure 560 may then End in block 670.

Figure 13:
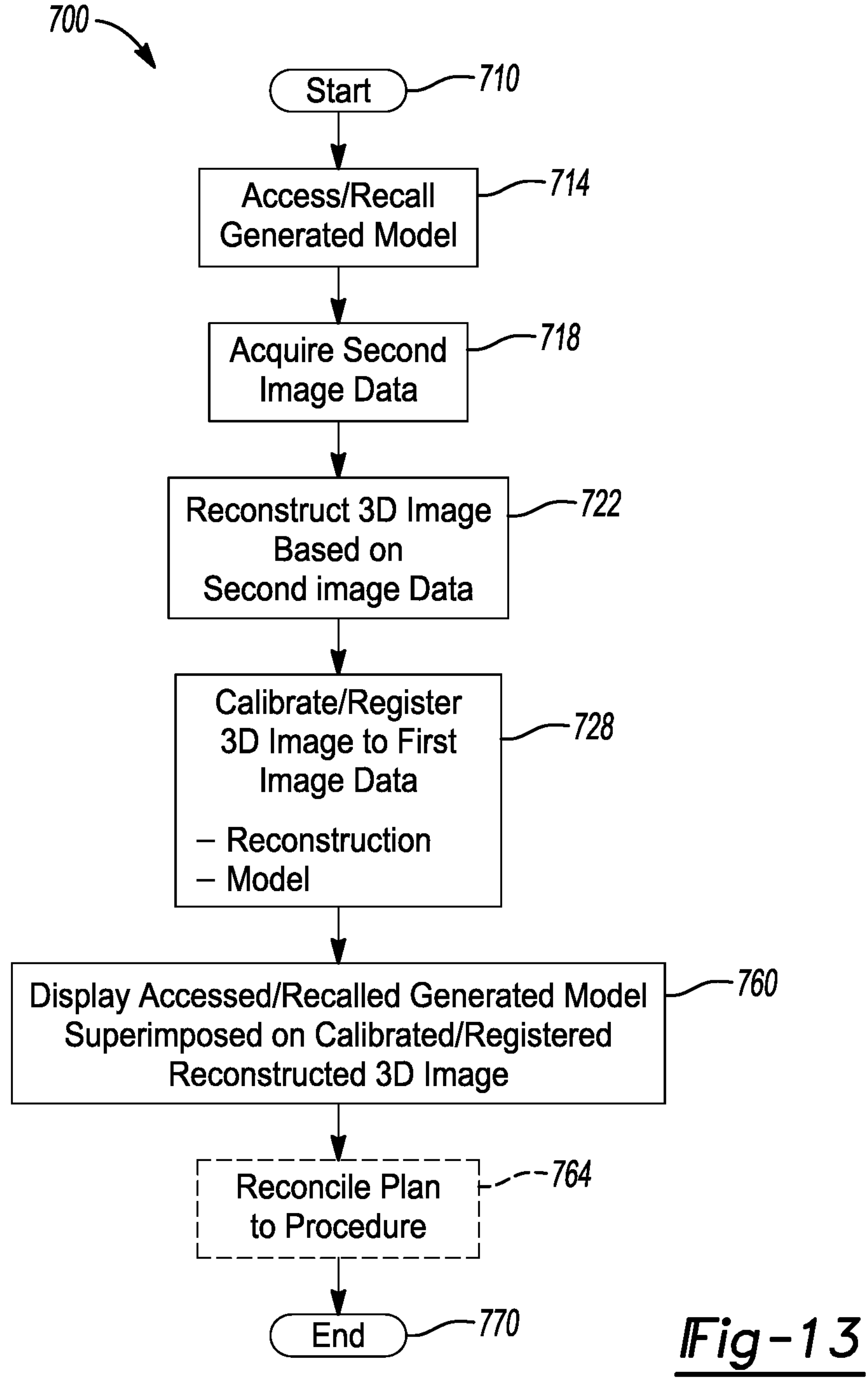
FIG. 13 is a flowchart for a process of reconciliation of a procedure to a model, according to various embodiments.
Figure 14:
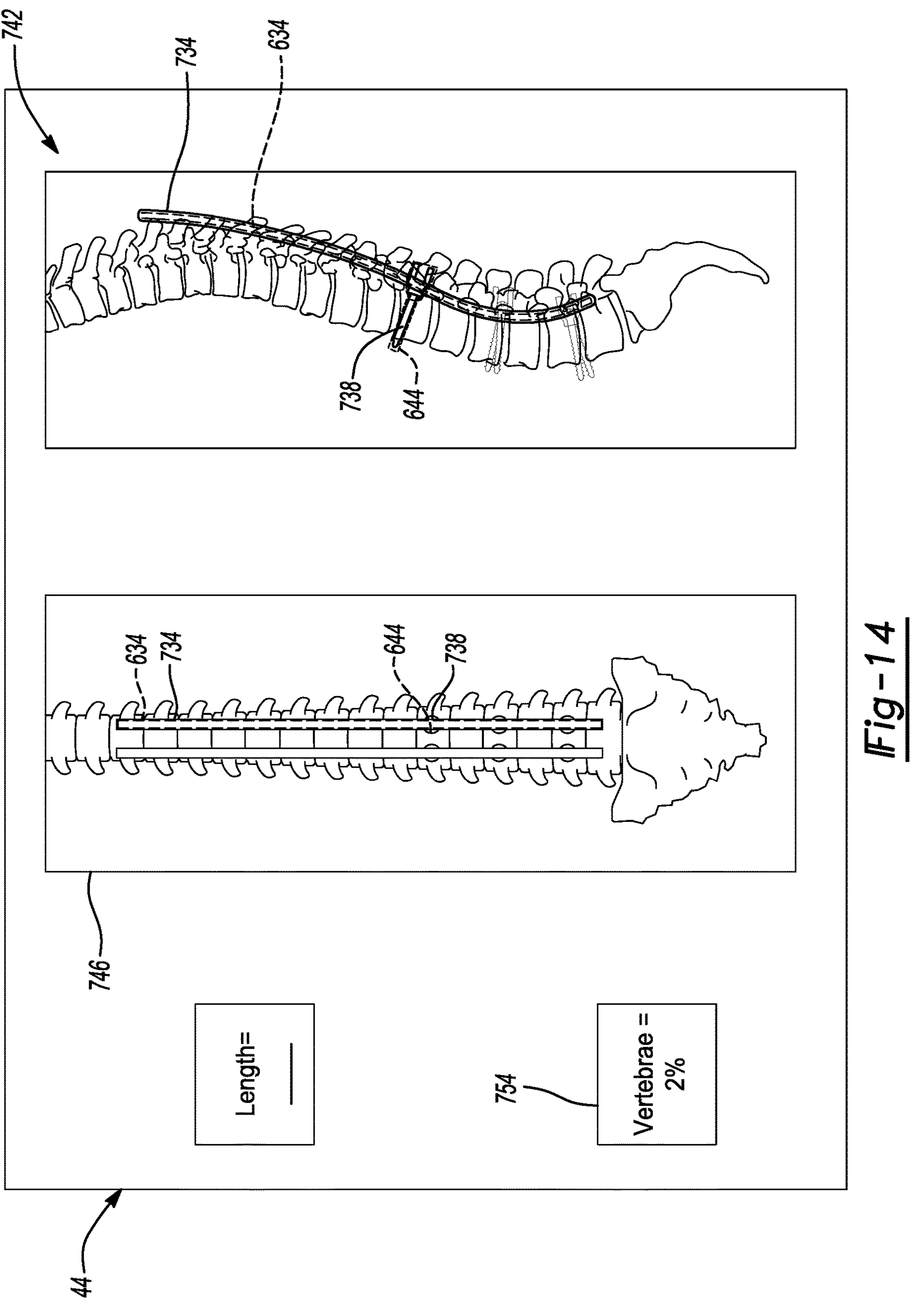
FIG. 14 is a graphical display of a model superimposed on an image of the subject, according to various embodiments.

Turning reference to FIG. 14 and FIG. 13, a procedure may be performed on the subject 28, similar to that discussed above. For example, a subject specific implant may be generated based upon the model that is generated as discussed above. The implant may include a rod for fixation of portions of the spine, such as one or more vertebrae 316 in the subject 28. The rod may be substantially unique to the subject may be used for procedure. Further, various fixation members may be used to assist in fixating the rod to the subject 28. Regardless the rod may be implanted into the subject in an appropriate manner, such as those understood by one skilled in the art. Once a rod is implanted or any appropriate implant is implanted a procedure may be reconciled to a plan and validated that the plan was achieved or variance therefrom.

With reference to FIG. 13, a process 700 is illustrated. The process 700 may be a validation process, which may be similar to the validation process 450 discussed above. The validation or reconciliation process 700 may begin and start Block 710. The generated model block 658 may be recalled or accessed in Start block 714. As discussed above the model may be saved for access at any appropriate time. Further the model may be generated and accessed substantially immediately such that it is not saved. Nevertheless, the model, such as including the rod model 634 and positions of the screws 644*a*, 644*b*, and any other appropriate features may be recalled in block 714.

Second image data may then be acquired in block 718. The acquired second image data may be any appropriate image data, such as image data acquired with the imaging system 26. The image data may be two-dimensional image data, three-dimensional image data, or other appropriate image data. According to various embodiments, three-dimensional image data may be generated by reconstructing a three-dimensional image based upon the image data acquired with the imaging system 26. Nevertheless, the image data may be acquired in any appropriate manner, such as with a CT scan, the alarm, or other appropriate as the imaging system 26.

If necessary, the reconstruction of a 3D image may be made in block 722. The reconstructed 3D image may be based upon the acquired second image data. The image data may be reconstructed in any appropriate manner, such as those discussed above.

The reconstructed image may then be calibrated and/or registered to the first image data in block 728. The calibration and/or registration of the reconstructed image or the second acquired image data to the first image data may be a registration of the second image data to the first image data, a matching of the calibration using the calibration member 310, as discussed above, or the like. The reconstructed image data may be a model based upon the second image data acquired in block 719 or may be a reconstruction of the image of the subject 28 based upon the acquired image data. The reconstructed 3D image of block 722 and/or the calibrated image from block 728 may be displayed on the display device 44. The reconstructed image may include an image that includes image data of the implant portions, including an implanted rod 734 and one or more implanted screws 738. The image of the rod 734 and the image of the screw 738 may be displayed with the image data of the subject. The display may include a 3D image and/or plurality of perspectives of the image, such as a medial-lateral view 742 and/or a posterior-to-anterior view 746. The one or more views may allow the user 28 to view the position of the implant, such as the rod with the x-ray rod image 734 for validation or reconciliation of the plan.

The generated model 634 may be overlaid, such as superimposed, on the x-ray images 742, 744. The rod model 634 may be overlaid on the image of the rod 734. Similarly in the planned positions of the screws 644 may be overlaid on the x-ray screw image 738. The overlays of the rod and screw 634, 644 may be overlaid in any number of the perspectives, such as in both of the images 742, 746. The display device 44 may also display various other outputs, such as a variance amount 754 or other appropriate output.

The superimposed model displayed on the acquired second image data may be displayed in block 760 and the display may be used by the user 24 to perform a reconciliation 764. The reconciliation may also be performed by the processor module, such as by executing instructions. The instructions may include determining an amount of alignment or malalignment of the rod model and screw models 634, 644 relative to the x-ray rod image 734 and the x-ray screw image 738. Further, as the image is segmented the position of the vertebrae may also be compared between the first image data and the reconstruction. Therefore, the reconciliation of the plan and the procedure may be performed by the processor module by determining an amount of alignment or shape of a vertebra or the vertebra orientation. The amount of alignment may include a determination of an edge-to-edge comparison between the various portions, such as the x-ray rod 734 and the rod model 634. As discussed above the calibration and the registration allows for the generated model to substantially match a predicted procedure for confirmation a reconciliation of the plan.

The procedure reconciliation may then End in block 770. The reconciliation may be used to determine and the success of the procedure and/or positioning of the implant relative to the plan.

The planning and procedure to perform a procedure on the subject 28 may occur according to various embodiments, including those discussed above, and further herein. It is understood that various features may be combined from any of the various embodiments, including the image and processing, image analysis, and reconciliation analysis.

According to various embodiments, for example, a system and method for planning and reconciling a procedure is illustrated in FIG. 15, FIG. 16, FIG. 17, and FIG. 18. A process 800 may Start in block 804 and acquire first image data in block 808. The first image data may be any appropriate type of image data, including that discussed above. Accordingly, the image data may be 2D, 3D, or other appropriate image data. The image data may be reconstructed into an image in block 812 and the image may be segmented in block 316. The reconstruction and/or segmentation of the image may be optional. Nevertheless, according to various embodiments, the image or image data may be segmented to identify various features in the image, such as a vertebrae, as discussed above. The segmentation may include an automatic segmentation based upon executing instructions with a processor module to analyze the image data and/or manual input regarding segmentation features in the image.

Figure 15:
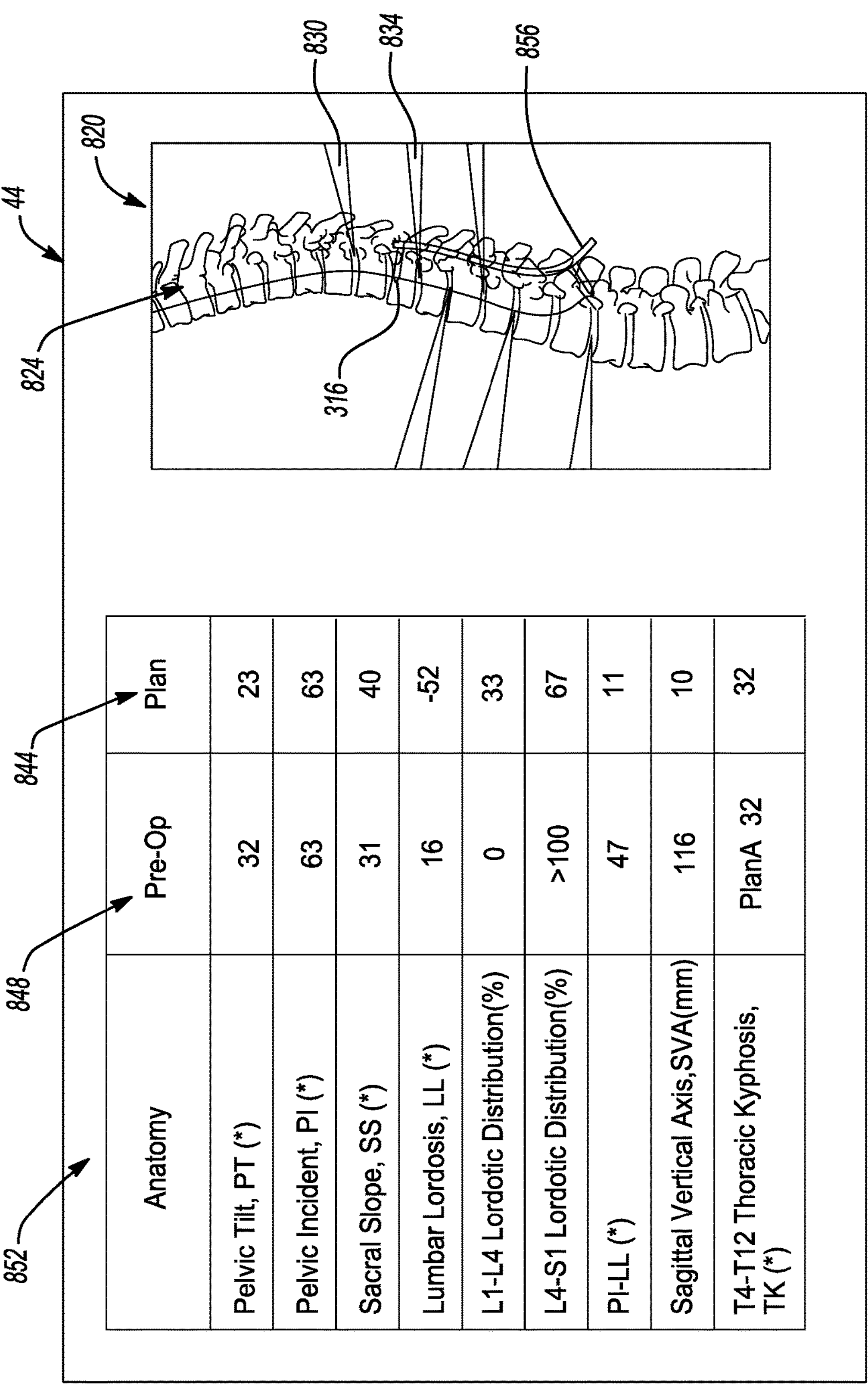
FIG. 15 is a graphical display of a plan and an image of the subject with the plan, according to various embodiments.
Figure 16:
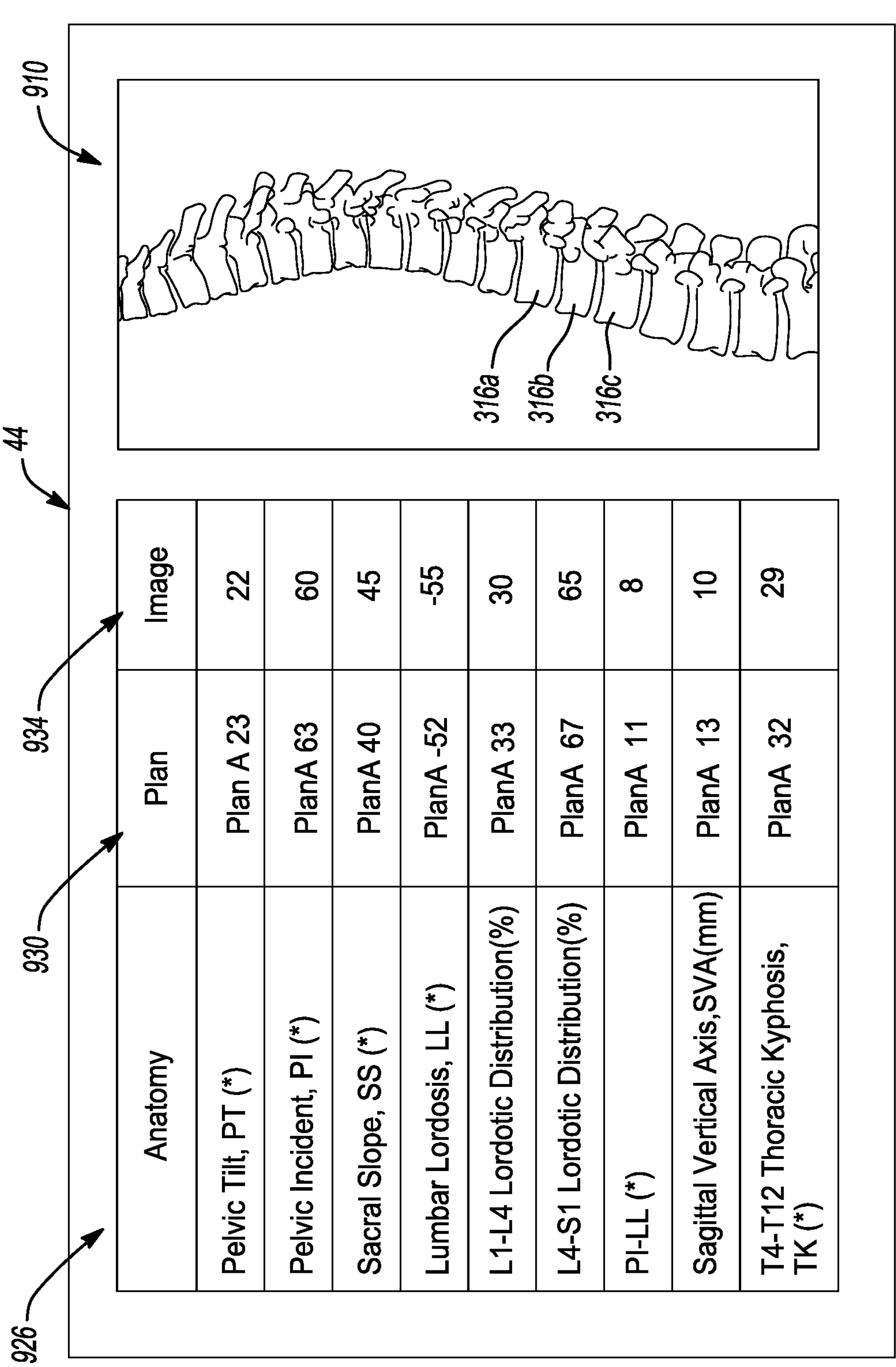
FIG. 16 is a graphical display of an image of the subject and a table of orientations of portions in the image, according to various embodiments.
Figure 17:
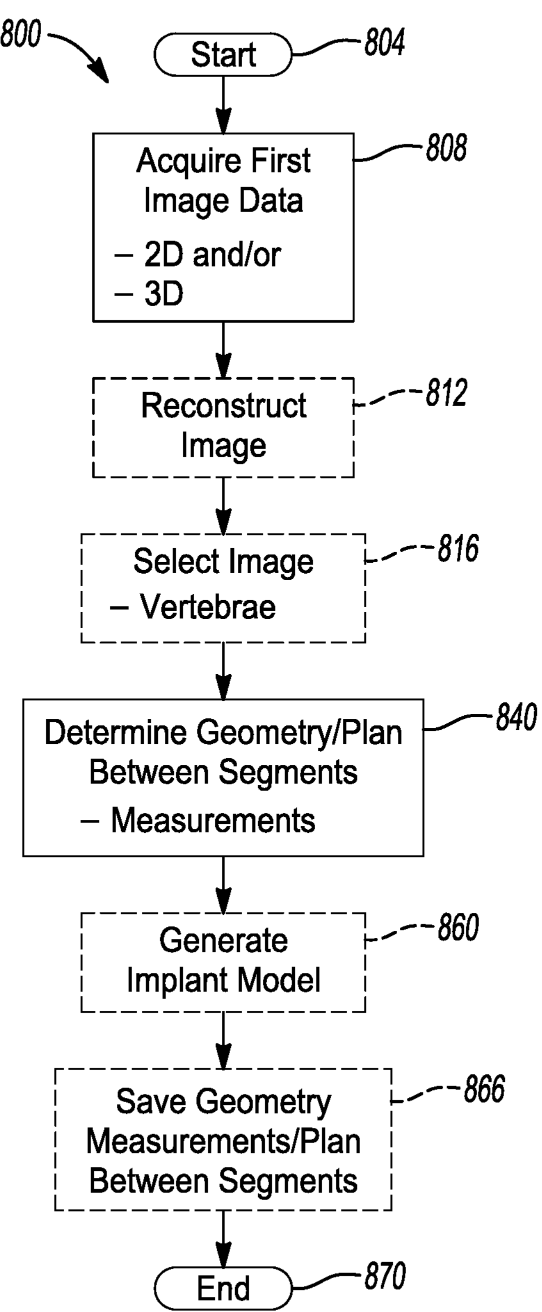
FIG. 17 is a flow chart of a process to generate a plan, according to various embodiments.

As illustrated in FIG. 15, an image may be displayed on the display device 44. The image 820 may include image data that is generated of the subject and displayed for viewing by the user. An implant planned for a procedure, including a selected geometry of various portions, such as a spine 824 and/or various vertebrae, such as the vertebrae 316. The areas of vertebrae and/or anatomical locations may be manipulated in the image 820 to generate a selected geometry or shape of the spine 824. As illustrated, movement or alignment of various portions of the image may cause open or dark areas in the image 830. Further various anatomical features, such as a transition point between the thoracic and lumbar vertebrae 834 may be identified.

Moving or aligning the segmented portions to a selected geometry or shape may occur in block 840 to determine a geometry of various portions of the anatomy that may be made and may be identified as a plan 844. A determined geometry or plan between the segments made in block 840 may be illustrated or displayed as the plan 844, including the various geometry planned to be achieved. The preoperative geometry may also be identified and displayed as a preoperative geometry in a table 848. The preoperative geometry and/or the plan geometry may be a plan or table 852 that may be displayed relative to the image 820. Thus, the user 24 may understand a current geometry and a plan geometry following a procedure.

A model of an implant may also be generated, if selected, including a rod model 856 in block 860. It is understood, however, that a model of an implant is not required. The determination of a plan geometry that is to be achieved may be generated and saved based upon the image data acquired of the subject in the plan. The plan may be performed or identified by the user 24 and/or based on selected constraints such as targeted alignment goals (e.g., Thoracic Kyphosis, Segmental angles) or targeted changes in vertebra location (e.g., orientation of the vertebra in a 3D plane).

Figure 18:
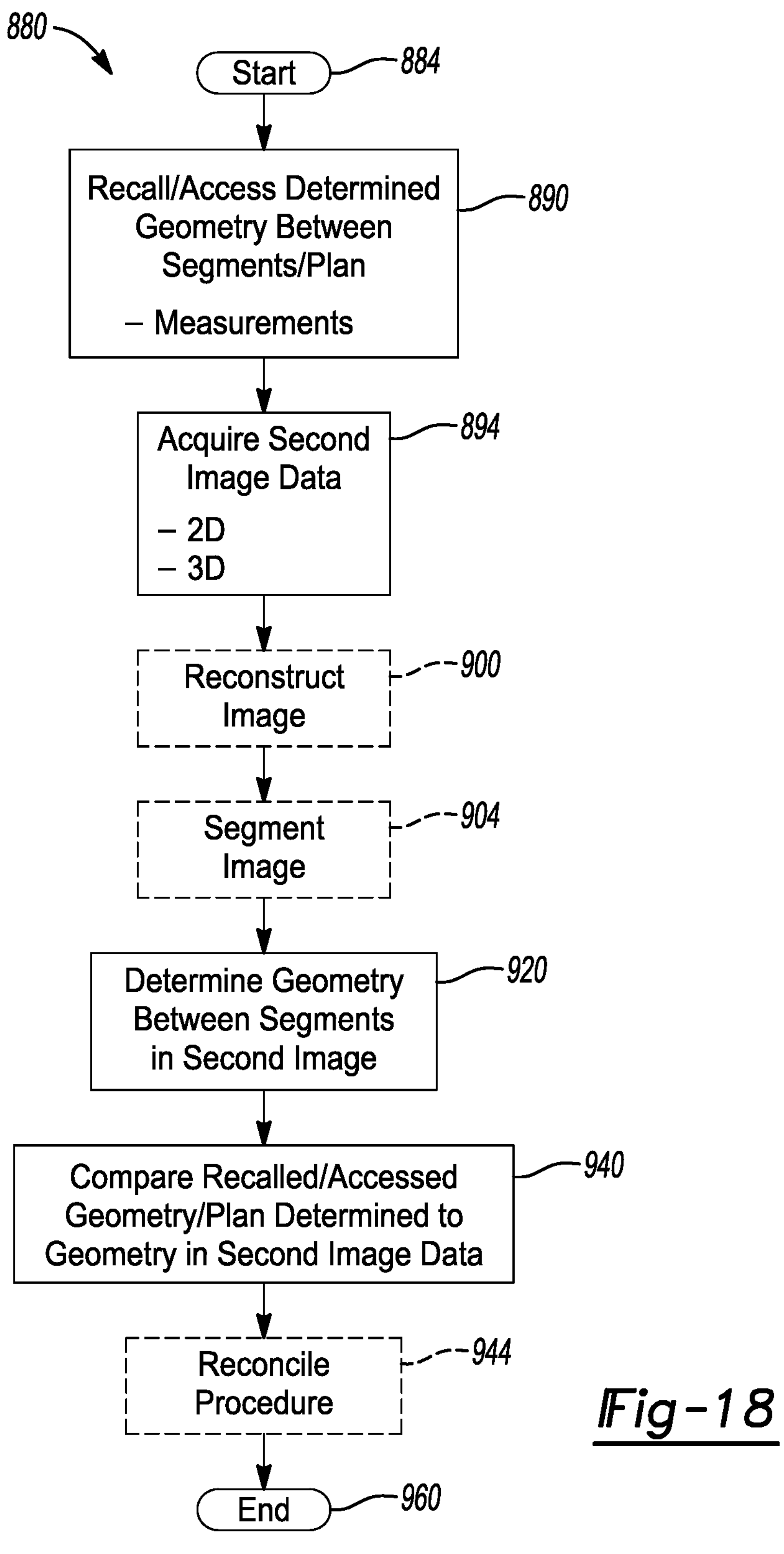
FIG. 18 is a flow chart of a process for reconciling a plan to a procedure, according to various embodiments.

The determined geometry or plan may be saved in block 866. The saving of the plan is optional and may not be required. Nevertheless, the determined geometry that is the plan may be used to identify and/or reconcile a procedure after the procedure is completed. The process 800 may then End in Block 870. The user 24 may then perform the procedure on the subject. A reconciliation process 380 is illustrated in FIG. 18.

The reconciliation process may begin in Start block 884 followed by recall and/or accessing a determined or plan geometry between segments in block 890. The procedure may be performed on the subject prior to acquiring a second image data in block 894. The second image data may be acquired of the subject in any appropriate manner, such as with the imaging system 36. As discussed above, the image data may be 2D image data, 3D image data, or any appropriate image data. The image data may be used to reconstruct an image in block 900. Further, the reconstructed image may be segmented in block 904. The image data and reconstructed image or model may be displayed on the display device 44 as the second image data or second reconstructed image data 910. The second image data may include the various portions, such as one or more segmented or identified vertebrae 316*a*, 316*b*, and 316*c*.

A geometry between the segments can be identified or determined in the second image in block 920. The determine geometry may be displayed, if selected, on the display device 44 in a table or comparison table 926 comparison table may include a column for the plan 930 and a second column for the image or actual 934. The plan geometry may be based on the recalled plan. The actual or image geometry may be determined at least form the second image data.

The second image data may include segmented portions and/or allow for an evaluation of angles of various portions therein. Therefore, the user 24 may identify elements or portions in the second image data and allow for measurements to be made between the elements, such as vertebrae. The angles therebetween and/or measurements in other anatomical regions may be compared to the plan. Thus, the second image data may be used for identifying geometry in the subject 28 after the procedure.

The comparison of the measured geometry may be used to determine or reconcile the plan to the procedure. Therefore, a comparison of the recalled/access geometry or plan to the determine geometry in the second image data is performed in block 940 and may allow for a reconciliation of the procedure and block that hundred and 44. The reconciliation may be performed by the user 24 by comparing or evaluating the determined geometry relative to the planned geometry. Further, the processor module may execute instructions to determine a variance between the planned geometry and the actual or image geometry. For example, validation or confirmation of a selected success may include removal of a 10° vertebra segment or changes in endplate angulation.

The reconciliation procedure 880 may then End in block 960. The reconciliation procedure 880 may be used to reconcile a procedure performed on the subject. The reconciliation need not require a calibration or measurement of the image data either in the first image data or in a second image data may allow for comparison between a first image data and second image data to determine whether a plan has been achieved or a comparison thereto. Thus the second image data may be evaluated to determine or reconcile a plan to a procedure or the result of the procedure.

As discussed above, a reconciliation of a procedure to a plan may be performed with image data acquired after or during a portion of a procedure. The procedure may include placing an implant and/or shaping a spine of a patient. The image data may be compared to a digital model based on a plan. The digital model may include a graphical representation of an implant and/or positions of portions of the subject, such as one or more vertebrae.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors or processor modules, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system to plan a procedure, comprising:

a processor module to execute instructions to:

access first image data of a subject having a calibration portion included in the first image data;

calibrate the first image data using the calibration portion included in the first image data;

segment the first image data into a first plurality of segments corresponding to a plurality of vertebrae of the subject;

determine, using the calibrated first image data, an implant geometry based on a planned positioning of the first plurality of segments;

access, after a portion of the procedure, second image data of the subject having an implant, the second image data having the calibration portion;

calibrate the second image data to a same calibration as the first image data using the calibration portion of the second image data;

segment the second image data into a second plurality of segments corresponding to the plurality of vertebrae of the subject;

identify a geometry between the second plurality of segments; and generate a graphical representation of the determined implant geometry to be superimposed on an image of the accessed second image data and the implant; and a display device configured to display a comparison table of the planned positioning of the first plurality of segments and the geometry between the second plurality of segments.

2. The system of claim 1, wherein the display device is further configured to display the second image data and the graphical representation superimposed on the displayed second image data.

3. The system of claim 1, further comprising:

an imaging system configured to acquire the second image data;

wherein the second image data is configured to be at least one of a two-dimensional image or to be reconstructed into a three-dimensional image.

4. The system of claim 1, wherein the processor module to execute instructions to calibrate the first image data comprises determining a dimension of a selected portion of the subject using the calibration portion.

5. The system of claim 4, wherein the processor module to execute instructions to determine the implant geometry based on the planned positioning of the portion in the first image data comprises determining a size and a geometry of a rod configured to achieve the planned positioning of the portion of the first image data.

6. The system of claim 5, wherein the processor module to execute instructions to generate the graphical representation of the determined implant geometry to be superimposed on the accessed second image data at the implant comprises generating the graphical representation based on a model of the rod having dimensions based on the calibration of the first image data and the second image data; and wherein a size and a geometry of the graphical representation based on the model is calibrated to a dimension of the second image data to illustrate a true position of the planned positioning.

7. The system of claim 1, wherein the processor module to execute instructions is further to:

receive an input to move the generated graphical representation superimposed on the image.

8. The system of claim 1, wherein the processor module to execute instructions to calibrate the second image data to the same calibration as the first image data comprises determining an equal dimension of a portion of the first image data and the second image data.

9. A system to plan a procedure, comprising:

a processor module to execute instructions to:

access first image data of a subject having a calibration portion included in the first image data;

reconstruct a first three-dimensional (3D) image of the subject with the accessed first image data;

calibrate the first 3D image using the calibration portion included in the first image data;

segment the first 3D image to generate a first plurality of segments corresponding to a plurality of vertebrae of the subject;

determine a planned geometry of the first plurality of segments of the segmented first 3D image;

determine, using the calibrated first 3D image, a 3D implant geometry based on the planned geometry of the first plurality of segments;

access, after a portion of the procedure, second image data of the subject with an implant, the second image data having the calibration portion;

calibrate the second image data to a same calibration as the first image data using the calibration portion in the second image data;

reconstruct a second 3D image of the subject with the accessed second image data;

segment the second 3D image into a second plurality of segments corresponding to the plurality of vertebrae of the subject;

identify a geometry between the second plurality of segments; and generate a graphical representation of the determined 3D implant geometry to be superimposed on the reconstructed second 3D image; and a display device configured to display a comparison table of the planned geometry of the first plurality of segments and the geometry between the second plurality of segments.

10. The system of claim 9, wherein the display device is further configured to display the reconstructed second 3D image and the graphical representation of the determined 3D implant geometry.

11. The system of claim 9, further comprising:

an imaging system configured to acquire the second image data;

wherein the second image data is configured to be reconstructed into a 3-D image.

12. The system of claim 9, wherein the processor module to execute instructions to calibrate the first 3D image comprises determining a dimension of a selected portion of the subject in the first image data using the calibration portion.

13. The system of claim 12, wherein the processor module to execute instructions to determine the 3D implant geometry based on the planned geometry of the segments comprises determining a size and a geometry of a rod configured to achieve the planned geometry of the segments of the segmented first 3D image.

14. The system of claim 13, wherein the processor module to execute instructions to generate the graphical representation of the determined 3D implant geometry comprises generating the graphical representation based on a model of the rod having dimensions based on the segmented first 3D image; and wherein a size and a geometry of the graphical representation based on the model is calibrated to a dimension of the second image data to illustrate a true position of the planned geometry of the segments of the segmented first 3D image.

15. The system of claim 9, wherein the processor module is further to execute instructions to:

receive an input to move the generated graphical representation superimposed on the image.

16. The system of claim 9, wherein the processor module is further to execute instructions to:

calibrate the reconstructed second 3D image to a same calibration as the first 3D image, wherein calibrating the reconstructed second 3D image comprises determining an equal dimension of a portion of the first image data and the second image data.

17. A system to plan a procedure, comprising:

a processor module to execute instructions to:

access first image data of a subject having an initial geometry of a region of interest prior to a procedure and having a calibration portion included in the first image data;

calibrate the first image data using the calibration portion included in the first image data;

segment the first image data into a first plurality of regions of interest of the subject;

generate planned image data of the subject having a planned geometry of the first plurality of regions of interest subsequent to a procedure that is different than the initial geometry;

access second image data of the subject subsequent to the procedure, the second image data having the calibration portion;

calibrate the second image data to a same calibration as the first image data using the calibration portion in the second image data;

segment the second image data into a second plurality of regions of interest;

determine a subsequent geometry of the second plurality of regions of interest; and generate a graphical representation of the determined subsequent geometry; and a display device configured to display a comparison table of the planned geometry and the subsequent geometry.

18. The system of claim 17, wherein the display device is further configured to display the graphical representation of the determined subsequent geometry including at least a representation of the determined subsequent geometry to be viewed by a user.

19. The system of claim 17, wherein the processor module to execute instructions to generate the planned image data of the subject includes determining the planned geometry includes at least an angle between a first vertebra and a second vertebra.

20. The system of claim 17, wherein the processor module executes further instructions to:

compare the determined subsequent geometry of the second plurality of regions of interest to the planned geometry of the first plurality of regions of interest.

* * * * *